United States Patent
Greatrex et al.

(10) Patent No.: US 11,384,094 B2
(45) Date of Patent: Jul. 12, 2022

(54) CHIRAL AUXILIARIES AND USES THEREOF

(71) Applicant: Ben William Greatrex, Black Mountain (AU)

(72) Inventors: Ben William Greatrex, Armidale (AU); Julian Klepp, Armidale (AU)

(73) Assignee: Ben Greatrex, Black Mountain (AU)

( * ) Notice: Subject to any disclaimer, the term of this patent is extended or adjusted under 35 U.S.C. 154(b) by 141 days.

(21) Appl. No.: 16/651,187

(22) PCT Filed: Sep. 26, 2018

(86) PCT No.: PCT/AU2018/051051
§ 371 (c)(1),
(2) Date: Mar. 26, 2020

(87) PCT Pub. No.: WO2019/060953
PCT Pub. Date: Apr. 4, 2019

(65) Prior Publication Data
US 2020/0270267 A1  Aug. 27, 2020

(30) Foreign Application Priority Data
Sep. 26, 2017  (AU) ............................... 2017903898

(51) Int. Cl.
| | | |
|---|---|---|
| *C07D 493/08* | (2006.01) |
| *B01J 27/08* | (2006.01) |
| *B01J 27/125* | (2006.01) |
| *B01J 27/135* | (2006.01) |
| *B01J 31/14* | (2006.01) |

(52) U.S. Cl.
CPC ............ *C07D 493/08* (2013.01); *B01J 27/08* (2013.01); *B01J 27/125* (2013.01); *B01J 27/135* (2013.01); *B01J 31/143* (2013.01)

(58) Field of Classification Search
None
See application file for complete search history.

(56) References Cited

FOREIGN PATENT DOCUMENTS

| | | |
|---|---|---|
| EP | 0 229 034 A3 | 7/1987 |
| JP | 05279281 A * | 10/1993 |
| WO | WO 2014/055474 A1 | 4/2014 |

OTHER PUBLICATIONS

English translation of Patent No. JPH05279281A, Oct. 16, 1993; pp. 1-7 (Year: 1993).*
Grindley, T. et al. "Syntheses of 3-deoxy-3-substituted-D-glucose derivatives. Part I. Improvements in preparations of and nucleophilic additions to 1,6:2,3-dianhydro-4-O-benzyl-β-D-allopyranose" Canadian Journal of Chemistry (1987), 65(5), 1065-71 (Year: 1987).*
Biktagirov, I., et al., "Synthesis of α-Bromoisolevoglucosenone and its Cyclopenta Annulation," Russian Journal of Organic Chemistry, 2014, vol. 50, No. 9, pp. 1317-1322.
Blattner, R., et al., "2-Benzyloxy-6,8-dioxabicyclo[3.2.1]octanes: New Carbohydrate-derived Herbicides," Pestic. Sci. 1991, 31,419-435.

(Continued)

*Primary Examiner* — Medhanit W Bahta
(74) *Attorney, Agent, or Firm* — Knobbe, Martens, Olson & Bear, LLP

(57) ABSTRACT

The present invention relates to chiral auxiliaries and the syntheses thereof and uses thereof.

13 Claims, 1 Drawing Sheet

(56) References Cited

OTHER PUBLICATIONS

Cardona, F., et al., "Nitrone Cycloadditions to Isolevoglucosenone: Ready Access to a New Class of Directly Linked (1→3)-Imino-C-disaccharides", Organic Letters, 2003, vol. 5, No. 9, 1475-1478.
International Search Report, PCT/AU2018/051051, dated Dec. 10, 2018.
Markovic, D., et al., "Polysulfones: solid organic catalysts for the chemoselective cleavage of methyl-substituted allyl ethers under neutral conditions," Chem. Commun. 2004, pp. 2444-2445.
Marquis, C., et al., "Synthesis of (1→3)-C and HOMO(1→3)-C-Linked Imino-Disaccharides Starting from Levoglucosenone and Isolevoglucosenone," Heterocycles, vol. 56, 2002, pp. 181-208.
Mikkelsen, L., et al., Application of the Anomeric Samarium Route for the Convergent Synthesis of the C-Linked Trisaccharide α-D-Man-(1→3)- [ α-D-Man-(1-→6)]-D-Man and the Disaccharides α-D-Man-(1-→3)-[-D-Man and α-D-Man (1-→6)-D-Man, J. Org. Chem. 2002, 67, 6297-6308.
Sakuda, S., et al., "Assignment of the absolute configuration of blasticidin A and revision of that of aflastatin A", Tetrahedron Letters 48 (2007) 2527-2531.
Stockton, K., et al., Palladium-Catalyzed Suzuki-Miyaura, Heck and Hydroarylation Reactions of (-)-Levoglucosenone and Application to the Synthesis of Chiral γ-Butyrolactones, Eur. J. Org. Chem. 2015, 6999-7008.
Zanardi, M., et al., Synthesis of a simple chiral auxiliary derived from levoglucosenone and its application in a Diels-Alder reaction, Tetrahedron Letters 50 (2009) 999-1002.

* cited by examiner

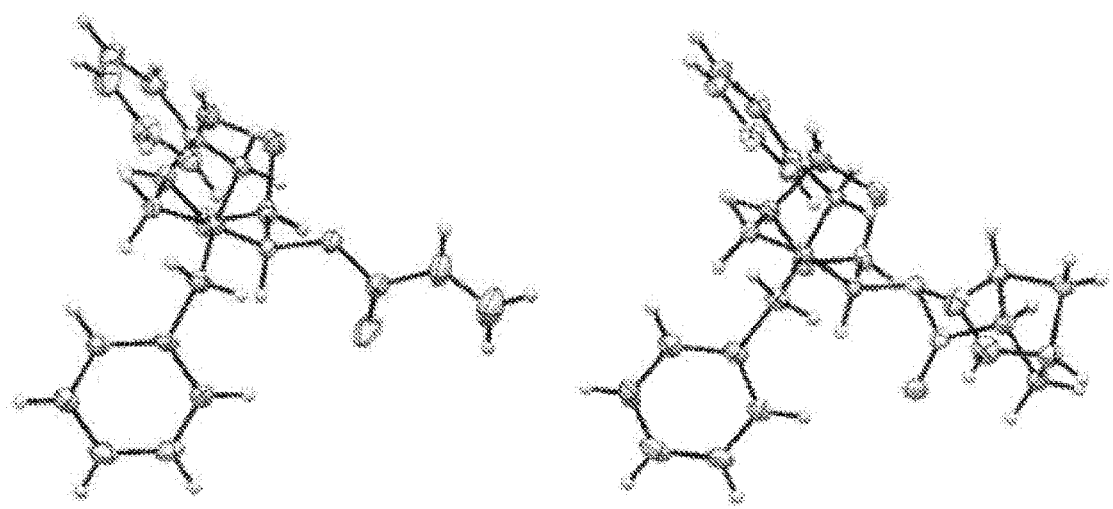

CHIRAL AUXILIARIES AND USES THEREOF

FIELD OF INVENTION

The present invention relates to chiral auxiliaries and the syntheses thereof and uses thereof.

BACKGROUND

Asymmetric or enantioselective chemical synthesis allows for optically active compounds with chirality to be produced. As one enantiomer or diastereomer of a compound may show greater or more desirable activity over its opposite counterpart in biological applications, for example, synthetic steps that lead to the preferential formation of a particular enantiomer or diastereomer is desired. Techniques exist to separate single enantiomers from a mixture, however this approach is less efficient since the other unwanted enantiomer is also produced and often discarded. As a result, the direct synthesis of the desired enantiomer or diastereomer through asymmetric synthesis is favoured over the use of separation techniques.

Asymmetric synthesis may be achieved using various approaches, one of which is through the use of a chiral auxiliary. A chiral auxiliary is a group or fragment that is attached to a substrate, which then controls the formation of one or more new stereocentres in the substrate during the reaction. The chiral auxiliary is typically incorporated into the substrate prior to the substrate-auxiliary complex being subjected to the reaction. In addition to controlling the formation of stereocentres, the use of a chiral auxiliary can allow for the easier separation of any resultant enantiomer or diastereomer.

Examples of chiral auxiliaries used in the field include 8-phenylmenthol, BINOL and various substituted oxazolidinones. These chiral auxiliaries and their derivatives have been used in various asymmetric reactions, however the compounds themselves often involve complex and costly syntheses. Additionally, the degree of control that a particular chiral auxiliary can impart may vary from one reaction to another.

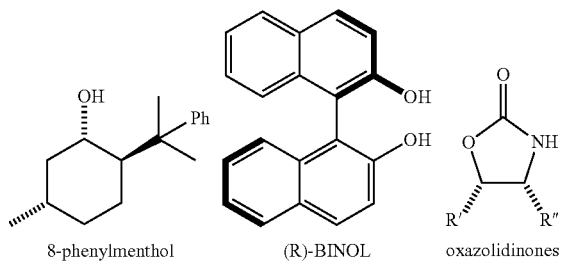

8-phenylmenthol  (R)-BINOL  oxazolidinones

Chiral auxiliaries typically control the stereochemical outcome of a transformation by generating interactions within the substrate, such that a particular side of the substrate is shielded and protected from the approach of reactants during the reaction. Chiral auxiliaries have been used to control the stereochemical outcome of various types of reactions, including cycloadditions, 1,2-additions, 1,4-additions, oxidations and reductions. While subsequent separation procedures after the use of such an auxiliary may be simplified, the initial use of a chiral auxiliary is often considered unfavourable as the overall atom economy is low, since a stoichiometric amount of the chiral auxiliary is required and additional steps are often required to install and remove the auxiliary from the substrate. Additionally, existing chiral auxiliaries may not provide the requisite selectivity or control for a particular synthetic reaction. Unlike the present invention, current strategies to synthesise chiral auxiliaries also use expensive raw materials, and involve lengthy and multiple separation and reduction steps, such as separation of diastereomers and resolution of enantiomers.

Alternatively, chiral auxiliaries may be used in chiral resolution to separate an enantiomer from a mixture. Chiral resolving agents are added to a mixture of enantiomers, such that a mixture of diastereomers is then formed as a result of a reaction between the resolving agent and each enantiomer. Given the difference in physical properties of diastereomers, subsequent separation using one or more physical methods allows for a single enantiomer of the original mixture to be obtained. The use of a chiral resolving agent as an approach for the separation of enantiomers may also be considered unfavourable, as a stoichiometric amount of the resolving agent is required, with other factors, such as solvent choice and solubility of the resolving agent and the substrate also to be considered. Examples of chiral resolving agents used in the field include tartaric acids, substituted amino acids, binaphthyl-like compounds and other such compounds.

Accordingly, there is a need for alternative chiral auxiliaries that are easy and cost-effective to produce and can effectively control the stereochemical outcome of a reaction. There is also a need for alternatives to known chiral resolving agents that allow for more efficient separation of individual enantiomers from a mixture of enantiomers.

SUMMARY OF THE INVENTION

In one aspect, the present invention provides an enantiomerically enriched compound of the general formula (I):

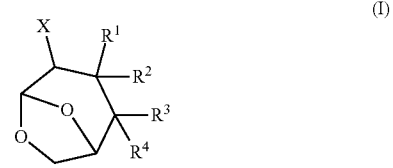

or a salt thereof, wherein:

$R^1$ and $R^2$, where present, may be the same or different and are selected from the group consisting of H, optionally substituted alkyl, optionally substituted aryl, optionally substituted heteroaryl, optionally substituted heterocyclyl, optionally substituted arylalkyl, optionally substituted heterocyclylalkyl, optionally substituted heteroarylalkyl, optionally substituted alkenyl, and optionally substituted alkynyl; or $R^1$ and $R^2$ taken together form a spirocyclic group;

$R^3$ and $R^4$, where present, may be the same or different and are selected from the group consisting of H, optionally substituted alkyl, optionally substituted alkenyl, optionally substituted alkynyl, optionally substituted aryl, optionally substituted heteroaryl, optionally substituted heterocyclyl, optionally substituted heteroarylalkyl, optionally substituted benzyl, optionally substituted silyl, optionally substituted acyl, optionally substituted alkoxy and NR$^5$R$^6$;

wherein at least one of R$^1$, R$^2$, R$^3$ and R$^4$ is not H;

R$^5$ and R$^6$ may be the same or different and are selected from the group consisting of H, optionally substituted aryl, optionally substituted alkyl and SO$_2$R$^7$;

R$^7$ is H, alkyl or aryl;

X is NHR$^8$, OR$^8$ or SR$^8$; and

R$^8$ is H or comprises a prochiral reactive group.

In an embodiment of the first aspect, the present invention provides an enantiomerically enriched compound of the general formula (I):

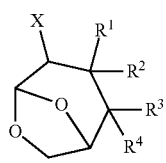

(I)

or a salt thereof, wherein:

R$^1$ and R$^2$, where present, may be the same or different and are selected from the group consisting of H, optionally substituted alkyl, optionally substituted aryl, optionally substituted heteroaryl, optionally substituted heterocyclyl, optionally substituted arylalkyl, optionally substituted heterocyclylalkyl, optionally substituted heteroarylalkyl, optionally substituted alkenyl, and optionally substituted alkynyl; or R$^1$ and R$^2$ taken together form a spirocyclic group;

R$^3$ and R$^4$, where present, may be the same or different and are selected from the group consisting of H, optionally substituted alkyl, optionally substituted alkenyl, optionally substituted alkynyl, optionally substituted aryl, optionally substituted heteroaryl, optionally substituted heterocyclyl, optionally substituted heteroarylalkyl, optionally substituted benzyl, optionally substituted silyl, optionally substituted acyl, optionally substituted alkoxy and NR$^5$R$^6$;

wherein at least one of R$^1$, R$^2$, R$^3$ and R$^4$ is not H;

R$^5$ and R$^6$ may be the same or different and are selected from the group consisting of H, optionally substituted aryl, optionally substituted alkyl and SO$_2$R$^7$;

R$^7$ is H, alkyl or aryl;

X is NHR$^8$, OR$^8$ or SR$^8$; and

R$^8$ is H, optionally substituted acyl, optionally substituted alkenylacyl, optionally substituted alkyl or a protecting group.

In a further embodiment of the first aspect, the present invention provides an enantiomerically enriched compound of the general formula (I):

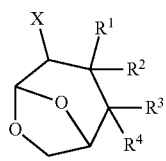

(I)

or a salt thereof, wherein:

R$^1$ and R$^2$, where present, may be the same or different and are selected from the group consisting of H, optionally substituted alkyl, optionally substituted aryl, optionally substituted heteroaryl, optionally substituted heterocyclyl, optionally substituted arylalkyl, optionally substituted heterocyclylalkyl, optionally substituted heteroarylalkyl, optionally substituted alkenyl, and optionally substituted alkynyl;

R$^3$ and R$^4$, where present, may be the same or different and are selected from the group consisting of H, optionally substituted alkyl, optionally substituted alkenyl, optionally substituted alkynyl, optionally substituted aryl, optionally substituted heteroaryl, optionally substituted heterocyclyl, optionally substituted heteroarylalkyl, optionally substituted benzyl, optionally substituted silyl, optionally substituted acyl, optionally substituted alkoxy and NR$^5$R$^6$;

wherein at least one of R$^1$, R$^2$, R$^3$ and R$^4$ is not H;

R$^5$ and R$^6$ may be the same or different and are selected from the group consisting of H, optionally substituted aryl, optionally substituted alkyl and SO$_2$R$^7$;

R$^7$ is H, alkyl or aryl;

X is NHR$^8$, OR$^8$ or SR$^8$;

R$^8$ is H, optionally substituted acyl, optionally substituted alkenylacyl, optionally substituted alkyl or a protecting group.

In another aspect, the present invention also provides an enantiomerically enriched compound of formula (I'):

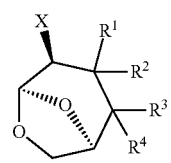

(I')

or a salt thereof, wherein

R$^1$ and R$^2$ may be the same or different and are selected from the group consisting of H, optionally substituted alkyl, optionally substituted aryl, optionally substituted heteroaryl, optionally substituted heterocyclyl, optionally substituted arylalkyl, optionally substituted heterocyclylalkyl, optionally substituted heteroarylalkyl, optionally substituted alkenyl, and optionally substituted alkynyl;

R$^3$ and R$^4$ may be the same or different and are selected from the group consisting of H, optionally substituted alkyl, optionally substituted alkenyl, optionally substituted alkynyl, optionally substituted aryl, optionally substituted heteroaryl, optionally substituted heterocyclyl, optionally substituted heteroarylalkyl, optionally substituted benzyl, optionally substituted silyl, optionally substituted acyl, optionally substituted alkoxy and NR$^5$R$^6$;

wherein at least one of R$^1$, R$^2$, R$^3$ and R$^4$ is not H;

R$^5$ and R$^6$ may be the same or different and are selected from the group consisting of H, optionally substituted aryl, optionally substituted alkyl and SO$_2$R$^7$;

R$^7$ is H, alkyl or aryl;

X is NHR$^8$, OR$^8$ or SR$^8$;

R$^8$ is H, optionally substituted acyl, optionally substituted alkenylacyl, optionally substituted alkyl or a protecting group.

According to a further aspect, the present invention also provides an enantiomerically enriched compound of formula (I"):

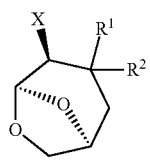

(I″)

or a salt thereof, wherein
R¹ and R² may be the same or different and are selected from the group consisting of H, optionally substituted alkyl, optionally substituted aryl, optionally substituted heteroaryl, optionally substituted heterocyclyl, optionally substituted arylalkyl, optionally substituted heterocyclylalkyl, optionally substituted heteroarylalkyl, optionally substituted alkenyl, and optionally substituted alkynyl;
wherein at least one of R¹ and R² is not H;
X is OR⁸; and
R⁸ is H, optionally substituted acyl, optionally substituted alkenylacyl, optionally substituted alkyl or a protecting group.

According to yet a further aspect, the present invention also relates to a process for preparing a compound of formula (I), (I') or (I″), wherein a compound of formula (II) or (IIa):

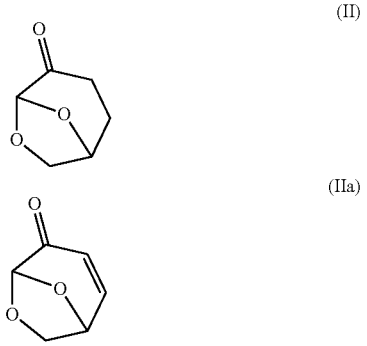

(II)

(IIa)

is reacted under conditions to provide a compound of formula (III), in which the variables R¹, R², R³ and R⁴ are as defined above,

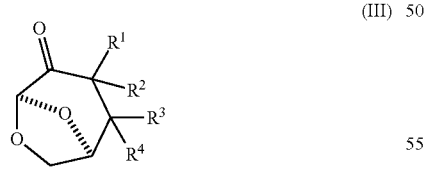

(III)

and the compound of formula (III) is reduced to provide a compound of formula (I), (I') or (I″).

According to another aspect, the present invention provides an enantiomerically enriched compound prepared according to an aspect as described herein.

According to another aspect, the present invention provides the use of an enantiomerically enriched compound according to an aspect of the present invention as a chiral auxiliary to control the stereochemical outcome of a cycloaddition or a conjugate addition reaction.

According to a further aspect, the present invention also provides the use of an enantiomerically enriched compound according to an aspect of the present invention as a chiral auxiliary to control the stereochemical outcome of a Diels-Alder reaction, wherein a suitable Lewis acid catalyst is preferentially used.

According to another aspect, the present invention provides the use of an enantiomerically enriched compound according to an aspect of the present invention as a resolving agent to separate an enantiomer of a compound from a mixture of its enantiomers.

According to another aspect, the present invention provides the use of an enantiomerically enriched compound according to an aspect of the present invention to determine the stereochemistry of another compound.

According to another aspect, the present invention provides the use of an enantiomerically enriched compound according to an aspect of the present invention to determine the enantiomeric excess of a mixture of chiral compounds.

BRIEF DESCRIPTION OF THE DRAWINGS

Preferred embodiments of the invention are hereafter described, by way of non-limiting example only, with reference to the accompanying drawings, in which:
The FIGURE is an example of the X-ray crystal structures of a compound of the present invention showing the accessible acrylate in the solid state and in the product.

DETAILED DESCRIPTION OF THE INVENTION

The present invention seeks to provide an enantiomerically enriched compound of general formula (I), which may be used to control the stereochemical outcome of a reaction. The present auxiliaries as defined by formula (I) advantageously displays excellent diastereoselectivity in Diels-Alder reactions and other addition reactions. The compounds of the present invention can also be synthesised in two to three steps from low cost starting materials without chromatography and using only BnBr/KOtBU/THF and NaBH₄/MeOH.

The following additional advantages of the present compounds have been realised for the first time by the inventors:
The chiral auxiliaries of the present invention can be prepared cheaply and efficiently from a renewable natural source (i.e. cellulose). For instance, it is proposed that the chiral auxiliaries of the present invention can be produced (on large scale) at up to only one hundredth the cost of producing the currently used auxiliary 8-phenylmenthol.
The chiral auxiliaries of the present invention can be utilised in various chemistries including cycloaddition and conjugate addition chemistry.
The chiral auxiliaries of the present invention are typically presented as highly crystalline solids and thus the addition salts are also highly crystalline leading to easily resolvable enantiomers when used as resolving agents.

As used herein, the term "enantiomerically enriched" means that the compound is in a form such that there is more of the enantiomer of general formula (I) than its enantiomeric pair. Such enantiomerically enriched chiral compounds display optical activity.

As used herein, the term "enantiomerically pure" means that the enantiomer is substantially free of its enantiomeric pair. Enantiomeric purity is generally expressed in terms of enantiomeric excess or % ee. For a pair of enantiomers, (+) and (−), wherein the mixture of the two enantiomers is given as the mole or weight fractions $F_+$ or $F_-$ and wherein the sum of $F_+$ and $F_-$ is 1, the enantiomeric excess is defined as the difference of $F_+$ and $F_-$. Accordingly, the enantiomeric excess is expressed as a percentage, i.e. $(F_+-F_-)\times 100$. As used herein, the term "enantiomerically pure" means that the % ee is greater than 70%. Preferably, the % ee is greater than about 85%, about 88%, about 90%, about 92% or about 94%. More preferably, the % ee is greater than about 95%. In certain embodiments, the compounds of general formula (I) of the present invention are utilised in enantiomerically pure form.

"Alkyl" refers to a monovalent alkyl groups that may be straight chained or branched, and preferably have from 1 to 10 carbon atoms, or more preferably 1 to 6 carbon atoms. Examples of such groups include methyl, ethyl, n-isopropyl, iso-propyl, n-butyl, iso-butyl, n-hexyl, and the like.

"Alkenyl" refers to a monovalent aliphatic carbocyclic group having at least one carbon-carbon double bond and which may be straight chained or branched, preferably having from 2 to 10 carbon atoms. Examples of such groups include a vinyl or ethenyl group (—CH═CH$_2$), n-propenyl (—CH$_2$CH═CH$_2$), iso-propenyl (—C(CH$_3$)═CH$_2$), but-2-enyl (—CH$_2$CH═CHCH$_3$), and the like.

"Alkynyl" refers to a monovalent aliphatic carbocyclic group having at least one carbon-carbon triple bond and which may be straight chained or branched, preferably having from 2 to 10 carbon atoms. Examples of such groups include an acetylene or ethynyl group (—C≡CH), propargyl (—CH$_2$C≡CH), and the like.

"Acyl" refers to a group containing a carbonyl (—C═O) group, i.e. an oxygen atom attached to a carbon atom by a double bond. Examples of such groups include a formyl group (—COCH$_3$), an acetyl group (—COCH$_2$CH$_3$) or a benzoyl group (—COCH$_2$Ph).

"Alkenylacyl" refers to a group containing an acyl group (i.e. a carbonyl-containing group) attached to an alkene, which may be further substituted. The alkenylacyl group may also be an acyl group that is unsaturated at the alpha and beta positions. Examples of an alkenylacyl group include an acrylate group (—COCH═CH$_2$), a methacrylate group (—COCH═CHCH$_3$) and a cinnamate group (—COCH═CHPh).

"Aryl" refers to a monovalent unsaturated aromatic carbocyclic group having a single ring (e.g. phenyl) or multiple condensed rings (e.g. naphthyl, anthracenyl), preferably having from 6 to 14 carbon atoms. Examples of aryl groups include phenyl, naphthyl, anthracenyl and the like.

"Alkoxy" and "aryloxy" refers to the groups "—O-alkyl" and "—O-aryl", respectively, wherein the alkyl and aryl groups are described above.

"Heteroaryl" refers to a monovalent aromatic carbocyclic group, preferably having from 6 to 14 carbon atoms and 1 to 4 heteroatoms, wherein the heteroatoms are within the ring and are selected independently from oxygen, nitrogen and sulfur. Such heteroaryl groups can have a single ring (e.g. pyridyl, pyrrolyl or furyl) or multiple condensed rings (e.g. indolyl and benzofuryl).

"Heterocyclyl" refers to a monovalent saturated or unsaturated group having a single ring or multiple condensed rings, preferably having from 4 to 10 carbon atoms and from 1 to 4 heteroatoms, wherein the heteroatoms are selected independently from nitrogen, sulfur, oxygen, selenium and phosphorus.

Examples of heterocyclyl and heteroaryl groups include, but are not limited to pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, piperidinyl, pyrrolidine, tetrahydrofuranyl, and the like.

"Arylalkyl" refers to -alkylene-aryl groups preferably having from 1 to 10 carbon atoms in the alkylene moiety and from 6 to 10 carbon atoms in the aryl moiety. Such arylalkyl groups are exemplified by benzyl, phenethyl and the like.

"Heteroarylalkyl" refers to the group heteroaryl-alkyl-wherein heteroaryl and alkyl are described as above.

"Heterocyclylalkyl" refers to the heterocyclyl-alkyl-group wherein the heterocyclyl group and alkyl group are as described above.

"Protecting group" as used herein means a temporary modification of a potentially reactive functional group which protects it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: New York, 1991).

As used herein, the term "optionally substituted" in relation to a particular group is taken to mean that the group may or may not be further substituted with one or more groups selected from hydroxyl, acyl, alkyl, alkoxy, alkenyl, alkenyloxy, alkynyl, alkynyloxy, amino, aminoacyl, alkylaryl, aryl, aryloxy, carboxyl, acylamino, cyano, halogen, nitro, sulphate, phosphate, phosphine, heteroaryl, heterocyclyl, oxyacyl, oxyacylamino, aminoacyloxy, trihalomethyl, and the like.

The term "spirocycle" refers to a group in a compound, where the compound comprises two or more rings and the group forming one of the rings is bound to the other ring through a single carbon atom.

The term "prochiral reactive group" refers to a group that may be subjected to a reaction that results in the group containing a chiral centre as a result of the reaction.

In an aspect, the present invention provides an enantiomerically enriched compound of the general formula (I):

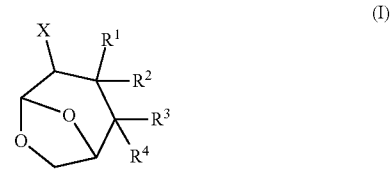

(I)

or a salt thereof, wherein:

$R^1$ and $R^2$, where present, may be the same or different and are selected from the group consisting of H, optionally substituted alkyl, optionally substituted aryl, optionally substituted heteroaryl, optionally substituted heterocyclyl, optionally substituted arylalkyl, optionally substituted heterocyclylalkyl, optionally substituted heteroarylalkyl, optionally substituted alkenyl, and optionally substituted alkynyl; or $R^1$ and $R^2$ taken together form an optionally substituted monocyclic group or an optionally substituted bicyclic group;

$R^3$ and $R^4$, where present, may be the same or different and are selected from the group consisting of H, optionally substituted alkyl, optionally substituted alkenyl, optionally substituted alkynyl, optionally substituted aryl, optionally substituted heteroaryl, optionally substituted heterocyclyl, optionally substituted heteroarylalkyl, optionally substituted benzyl, optionally substituted silyl, optionally substituted acyl, optionally substituted alkoxy and $NR^5R^6$;

wherein at least one of $R^1$, $R^2$, $R^3$ and $R^4$ is not H;

$R^5$ and $R^6$ may be the same or different and are selected from the group consisting of H, optionally substituted aryl, optionally substituted alkyl and $SO_2R^7$;

$R^7$ is H, alkyl or aryl;

X is $NHR^8$, $OR^8$ or $SR^8$; and $R^8$ is H or comprises a prochiral reactive group.

In some embodiments, one of $R^1$ and $R^2$ is H, optionally substituted aryl or optionally substituted arylalkyl. In other embodiments, one of $R^1$ and $R^2$ is optionally substituted benzyl. In other embodiments, one of $R^1$ and $R^2$ is optionally substituted benzyl, wherein $R^1$ and $R^2$ are each independently substituted with one or more alkyl groups. In other embodiments, one of $R^1$ and $R^2$ is optionally substituted benzyl, wherein $R^1$ and $R^2$ are each independently substituted with one or more halogen groups.

In an embodiment, both $R^1$ and $R^2$ are optionally substituted aryl. In another embodiment, both $R^1$ and $R^2$ are optionally substituted arylalkyl. In another embodiment, both $R^1$ and $R^2$ are optionally substituted benzyl. In other embodiments, both $R^1$ and $R^2$ are optionally substituted benzyl, wherein $R^1$ and $R^2$ are each independently substituted with one or more alkyl groups. In other embodiments, both $R^1$ and $R^2$ are optionally substituted benzyl, wherein $R^1$ and $R^2$ are each independently substituted with one or more halogen groups. In another embodiment, $R^1$ is a benzyl group optionally substituted with one or more alkyl groups while $R^2$ is a benzyl group optionally substituted with one or more halogen groups.

In an embodiment, $R^1$ and $R^2$ taken together form an optionally substituted monocyclic group. In another embodiment, $R^1$ and $R^2$ taken together form an optionally substituted bicyclic group. In some embodiments, the optionally substituted monocyclic or optionally substituted bicyclic group is a spirocyclic group. The monocyclic and bicyclic groups may be aromatic or non-aromatic. The monocyclic group may be carbocyclic, i.e. where the ring atoms are all carbon, or may comprise one or more heteroatoms. Examples of a monocyclic group include, but are not limited to cyclopropane, cyclobutane, cyclopentane, cyclohexane and cycloheptane.

The bicyclic group may also be carbocyclic and comprise carbon atoms in the rings. The bicyclic group may comprise a fused ring system. The bicyclic group may comprise an aromatic portion or be completely non-aromatic. Examples of a bicyclic group include, but are not limited to:

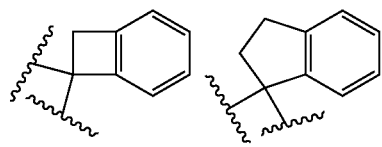

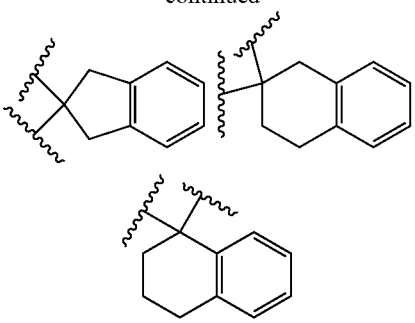

In an embodiment, one of $R^3$ and $R^4$ is H. In another embodiment, one of $R^3$ and $R^4$ is optionally substituted alkyl. In another embodiment, one of $R^3$ and $R^4$ is optionally substituted aryl. In another embodiment, one of $R^3$ and $R^4$ is optionally substituted heteroaryl. In another embodiment, one of $R^3$ and $R^4$ is optionally substituted heterocyclyl. In another embodiment, one of $R^3$ and $R^4$ is optionally substituted heteroarylalkyl. In another embodiment, one of $R^3$ and $R^4$ is optionally substituted arylalkyl. In another embodiment, one of $R^3$ and $R^4$ is optionally substituted silyl. In another embodiment, one of $R^3$ and $R^4$ is optionally substituted acyl. In another embodiment, one of $R^3$ and $R^4$ is optionally substituted alkoxy. In another embodiment, one of $R^3$ and $R^4$ is optionally substituted amino.

In an embodiment, one of $R^3$ and $R^4$ is optionally substituted benzyl. In another embodiment, one of $R^3$ and $R^4$ is $NR^5R^6$, wherein $R^5$ and $R^6$ may be the same or different and are selected from the group consisting of H, optionally substituted aryl, optionally substituted alkyl and $SO_2R^7$.

In some embodiments, both $R^3$ and $R^4$ are H. In some embodiments, both $R^3$ and $R^4$ are optionally substituted alkyl. In another embodiment, both $R^3$ and $R^4$ are optionally substituted aryl. In another embodiment, both $R^3$ and $R^4$ are optionally substituted heteroaryl. In another embodiment, both $R^3$ and $R^4$ are optionally substituted heterocyclyl. In another embodiment, both $R^3$ and $R^4$ are optionally substituted heteroarylalkyl. In another embodiment, both of $R^3$ and $R^4$ are optionally substituted arylalkyl. In another embodiment, both $R^3$ and $R^4$ are optionally substituted silyl. In another embodiment, both $R^3$ and $R^4$ are optionally substituted acyl. In another embodiment, both $R^3$ and $R^4$ are optionally substituted alkoxy. In another embodiment, both $R^3$ and $R^4$ are optionally substituted amino.

In some embodiments, both $R^3$ and $R^4$ are optionally substituted benzyl. In another embodiment, both $R^3$ and $R^4$ are $NR^5R^6$, wherein $R^5$ and $R^6$ may be the same or different and are selected from the group consisting of H, optionally substituted aryl, optionally substituted alkyl and $SO_2R^7$.

In an embodiment, X is $NHR^8$. In another embodiment, X is $OR^8$. In another embodiment, X is $SR^8$.

$R^8$ is H or comprises a prochiral reactive group. In an embodiment, $R^8$ is H, such that X is $NH_2$, OH or SH.

In an embodiment, $R^8$ comprises a prochiral reactive group. In an embodiment, $R^8$ comprises a functional group that is reactive under particular conditions and/or in the presence of another reagent or compound. In some embodiments, $R^8$ comprises a carbonyl group that is adjacent to the point of attachment to the chiral auxiliary, i.e. the group X. In an embodiment, $R^8$ is an optionally substituted acyl group. In another embodiment, $R^8$ is an optionally substituted alkenylacyl. In another embodiment, $R^8$ is an optionally substituted alkyl group. In another embodiment, $R^8$ is a protecting group.

In an embodiment, where X is O, the $R^8$ and X groups together form an ester functional group. In an embodiment, where X is N, the $R^8$ and X groups together form an amide functional group. In an embodiment, where X is S, the $R^8$ and X groups together form a thioester functional group.

The reactive functional group of $R^8$ may comprise an optionally substituted alkenylacyl. Without wishing to be bound by theory, the present inventors believe that the prochiral reactive group, for example an alkene (which bears a point of unsaturation), may undergo a variety of synthetic transformations, where the stereochemical outcome is influenced by the steric environment provided by the remainder of the chiral auxiliary. Examples of such transformations include, but are not limited to, cycloaddition reactions and conjugate addition reactions. An example of a cycloaddition reaction includes the Diels-Alder reaction between a diene and a dienophile (i.e. the alkene of $R^8$). An example of a conjugate addition reaction includes the Michael reaction between a nucleophile and an alpha,beta-unsaturated carbonyl compound. In the compounds of the present invention, the group $R^8$ is not strictly part of the chiral auxiliary but is the substrate that is attached to the chiral auxiliary and interacts in a manner such that the chiral auxiliary shields some part of the group $R^8$. This shielding in turn prevents the approach of an incoming reactant to the shielded part of $R^8$ and instead, forces the reactant to approach the unshielded part of $R^8$. This means that a particular side or face of the group $R^8$ is distinguished and the reaction between the prochiral reactive group and the incoming reactant occurs preferentially at the unshielded portion of the group $R^8$, thus resulting in a transformation that generates a chiral centre with a dominant stereochemistry.

Examples of alkenylacyl groups that may be represented by $R^8$ include, but are not limited to:

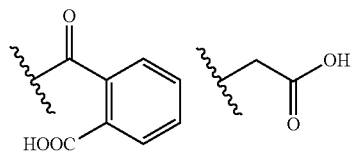

The present inventors have found that when $R^8$ is an optionally substituted acyl group, for example, an acyl group substituted with a carboxylic acid functional group, the chiral auxiliaries formed may be used as resolving agents. Without wishing to be bound by theory, the present inventors believe that a chiral auxiliary according to the present invention may be used to assist in determining the enantiomeric excess of a mixture of enantiomers. For example, a chiral auxiliary where the group $R^8$ comprises a carboxylic acid functionality can react with a suitable group on the substrate to be resolved. Reaction of the chiral auxiliary at the carboxylic acid group with the substrate produces a pair of diastereomers, which have physical characteristics that are sufficiently different to enable the enantiomeric excess of the mixture to be determined. Examples of such groups that may represent $R^8$ include, but are not limited to:

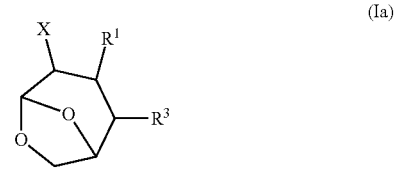

In some embodiments, the enantiomerically enriched compound of formula (I) is an enantiomerically pure compound of formula (I).

In an embodiment, at least one of $R^1$ or $R^2$ is present. In another embodiment, at least one of $R^3$ or $R^4$ is present. Accordingly, in an embodiment the present invention provides enantiomerically enriched compounds of formula (Ia):
or a salt thereof, wherein:

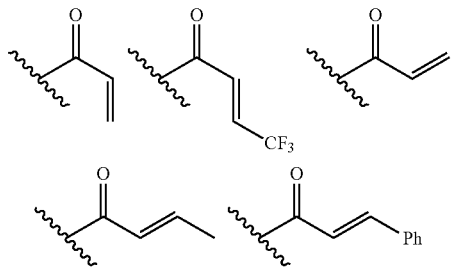

(Ia)

$R^1$ is selected from the group consisting of H, optionally substituted alkyl, optionally substituted aryl, optionally substituted heteroaryl, optionally substituted heterocyclyl, optionally substituted arylalkyl, optionally substituted heterocyclylalkyl, optionally substituted heteroarylalkyl, optionally substituted alkenyl, and optionally substituted alkynyl;

$R^3$ is selected from the group consisting of H, optionally substituted alkyl, optionally substituted alkenyl, optionally substituted alkynyl, optionally substituted aryl, optionally substituted heteroaryl, optionally substituted heterocyclyl, optionally substituted heteroarylalkyl, optionally substituted benzyl, optionally substituted silyl, optionally substituted acyl, optionally substituted alkoxy and $NR^5R^6$;

wherein at least one of $R^1$ and $R^3$ is not H;

$R^5$ and $R^6$ may be the same or different and are selected from the group consisting of H, optionally substituted aryl, optionally substituted alkyl and $SO_2R^7$;

$R^7$ is H, alkyl or aryl;

X is $NHR^8$, $OR^8$ or $SR^8$; and $R^8$ is H, optionally substituted acyl, optionally substituted alkenylacyl, or a protecting group.

In an embodiment, $R^1$ is H. In another embodiment, $R^3$ is H.

In some embodiments, the enantiomerically enriched compound of formula (Ia) is an enantiomerically pure compound of formula (Ia).

In an embodiment, $R^1$ and $R^2$ are independently selected from the group consisting of H, optionally substituted alkyl, optionally substituted aryl, optionally substituted heteroaryl, optionally substituted heterocyclyl, optionally substituted arylalkyl, optionally substituted heterocyclylalkyl, optionally substituted heteroarylalkyl, optionally substituted alkenyl, and optionally substituted alkynyl.

In some embodiments, one of $R^1$ and $R^2$ is H, optionally substituted aryl or optionally substituted arylalkyl. In other embodiments, one of $R^1$ and $R^2$ is optionally substituted arylalkyl. In other embodiments, one of $R^1$ and $R^2$ is optionally substituted benzyl. In other embodiments, one of $R^1$ and $R^2$ is optionally substituted benzyl, wherein $R^1$ and $R^2$ are each independently substituted with one or more alkyl groups. In other embodiments, one of $R^1$ and $R^2$ is optionally substituted benzyl, wherein $R^1$ and $R^2$ are each independently substituted with one or more halogen groups.

In another embodiment, $R^1$ and $R^2$ are both optionally substituted alkyl. In another embodiment, $R^1$ and $R^2$ are both optionally substituted aryl. In another embodiment, $R^1$ and $R^2$ are both optionally substituted heteroaryl. In another embodiment, $R^1$ and $R^2$ are both optionally substituted heterocyclyl. In another embodiment, $R^1$ and $R^2$ are both optionally substituted arylalkyl. In another embodiment, $R^1$ and $R^2$ are both optionally substituted heterocyclylalkyl. In another embodiment, $R^1$ and $R^2$ are both optionally substituted heteroarylalkyl. In another embodiment, $R^1$ and $R^2$ are both optionally substituted alkenyl. In another embodiment, $R^1$ and $R^2$ are both optionally substituted alkynyl.

In some embodiments, both $R^1$ and $R^2$ are optionally substituted benzyl. In other embodiments, both $R^1$ and $R^2$ are optionally substituted benzyl, wherein $R^1$ and $R^2$ are each independently substituted with one or more alkyl groups. In other embodiments, both $R^1$ and $R^2$ are optionally substituted benzyl, wherein $R^1$ and $R^2$ are each independently substituted with one or more halogen groups. In another embodiment, $R^1$ is a benzyl group optionally substituted with one or more alkyl groups while $R^2$ is a benzyl group optionally substituted with one or more halogen groups.

In an embodiment, one of $R^3$ and $R^4$ is H. In another embodiment, one of $R^3$ and $R^4$ is optionally substituted alkyl. In another embodiment, one of $R^3$ and $R^4$ is optionally substituted aryl. In another embodiment, one of $R^3$ and $R^4$ is optionally substituted heteroaryl. In another embodiment, one of $R^3$ and $R^4$ is optionally substituted heterocyclyl. In another embodiment, one of $R^3$ and $R^4$ is optionally substituted heteroarylalkyl. In another embodiment, one of $R^3$ and $R^4$ is optionally substituted arylalkyl. In another embodiment, one of $R^3$ and $R^4$ is optionally substituted silyl. In another embodiment, one of $R^3$ and $R^4$ is optionally substituted acyl. In another embodiment, one of $R^3$ and $R^4$ is optionally substituted alkoxy. In another embodiment, one of $R^3$ and $R^4$ is optionally substituted amino.

In an embodiment, one of $R^3$ and $R^4$ is optionally substituted benzyl. In another embodiment, one of $R^3$ and $R^4$ is $NR^5R^6$, wherein $R^5$ and $R^6$ may be the same or different and are selected from the group consisting of H, optionally substituted aryl, optionally substituted alkyl and $SO_2R^7$.

In some embodiments, both $R^3$ and $R^4$ are H. In some embodiments, both $R^3$ and $R^4$ are optionally substituted alkyl. In another embodiment, both $R^3$ and $R^4$ are optionally substituted aryl. In another embodiment, both $R^3$ and $R^4$ are optionally substituted heteroaryl. In another embodiment, both $R^3$ and $R^4$ are optionally substituted heterocyclyl. In another embodiment, both $R^3$ and $R^4$ are optionally substituted heteroarylalkyl. In another embodiment, both $R^3$ and $R^4$ are optionally substituted arylalkyl. In another embodiment, both $R^3$ and $R^4$ are optionally substituted silyl. In another embodiment, both $R^3$ and $R^4$ are optionally substituted acyl. In another embodiment, both $R^3$ and $R^4$ are optionally substituted alkoxy. In another embodiment, both $R^3$ and $R^4$ are optionally substituted amino.

In some embodiments, both $R^3$ and $R^4$ are optionally substituted benzyl. In another embodiment, both $R^3$ and $R^4$ are $NR^5R^6$, wherein $R^5$ and $R^6$ may be the same or different and are selected from the group consisting of H, optionally substituted aryl, optionally substituted alkyl and $SO_2R^7$.

In an embodiment, X is $NH_2$. In another embodiment, X is OH. In another embodiment, X is SH. In another embodiment, X is $NHR^8$, $OR^8$ or $SR^8$, wherein $R^8$ is optionally substituted acyl. In another embodiment, X is $NHR^8$, $OR^8$ or $SR^8$, wherein $R^8$ is optionally substituted alkenylacyl. In another embodiment, X is $NHR^8$, $OR^8$ or $SR^8$, wherein $R^8$ is a protecting group.

In another aspect, the present invention provides an enantiomerically enriched compound of formula (I'):
or a salt thereof, wherein

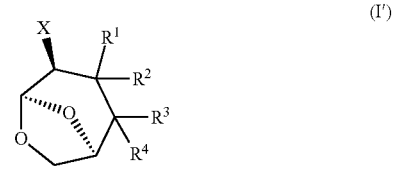

(I')

$R^1$ and $R^2$ may be the same or different and are selected from the group consisting of H, optionally substituted alkyl, optionally substituted aryl, optionally substituted heteroaryl, optionally substituted heterocyclyl, optionally substituted arylalkyl, optionally substituted heterocyclylalkyl, optionally substituted heteroarylalkyl, optionally substituted alkenyl, and optionally substituted alkynyl;

$R^3$ and $R^4$ may be the same or different and are selected from the group consisting of H, optionally substituted alkyl, optionally substituted alkenyl, optionally substituted alkynyl, optionally substituted aryl, optionally substituted heteroaryl, optionally substituted heterocyclyl, optionally substituted heteroarylalkyl, optionally substituted benzyl, optionally substituted silyl, optionally substituted acyl, optionally substituted alkoxy and $NR^5R^6$;

wherein at least one of $R^1$, $R^2$, $R^3$ and $R^4$ is not H;

$R^5$ and $R^6$ may be the same or different and are selected from the group consisting of H, optionally substituted aryl, optionally substituted alkyl and $SO_2R^7$;

$R^7$ is H, alkyl or aryl;

X is $NHR^8$, $OR^8$ or $SR^8$; and $R^8$ is H, optionally substituted acyl, optionally substituted alkenylacyl, or a protecting group.

In some embodiments, the enantiomerically enriched compound of formula (I') is an enantiomerically pure compound of formula (I').

In a further aspect, the present invention discloses an enantiomerically enriched compound of formula (I"):

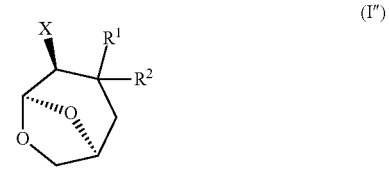

(I")

or a salt thereof, wherein $R^1$ and $R^2$ may be the same or different and are selected from the group consisting of H, optionally substituted alkyl, optionally substituted aryl, optionally substituted heterocyclyl, optionally substituted arylalkyl, optionally substituted heterocyclylalkyl, optionally substituted heteroarylalkyl, optionally substituted alkenyl, and optionally substituted alkynyl;

wherein at least one of $R^1$ and $R^2$ is not H;

X is $OR^8$; and $R^8$ is H, optionally substituted acyl, optionally substituted alkenylacyl, or a protecting group.

In an embodiment, $R^1$ and $R^2$ are independently selected from H, optionally substituted aryl, or optionally substituted arylalkyl. Preferably, $R^1$ and $R^2$ are independently selected from H and optionally substituted arylalkyl. Even more preferably, $R^1$ and $R^2$ are independently selected from H and optionally substituted benzyl. The optional substitution may be, but is not limited to, one or more of the following from which the substituting group is independently selected: halogen, or optionally substituted alkyl.

Accordingly, in some embodiments, $R^1$ and/or $R^2$ may be optionally substituted by $C_1$-$C_5$ alkyl, methyl, ethyl, n-propyl, isopropyl, n-butyl, chloro, fluoro, or bromo.

Accordingly, examples of compounds of formula (I") are represented below:

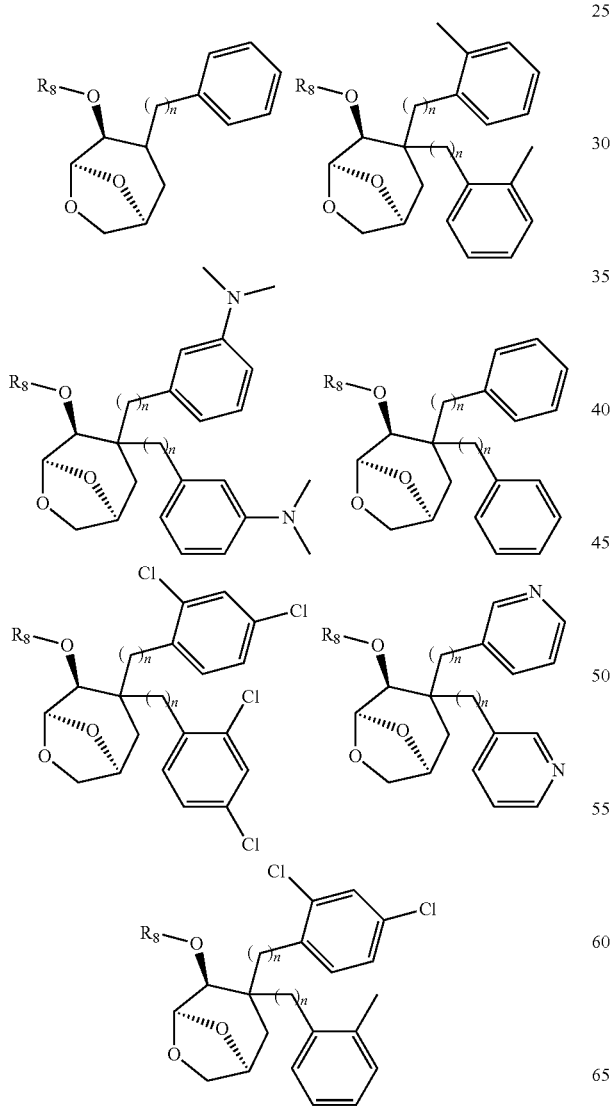

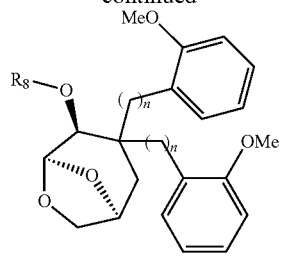

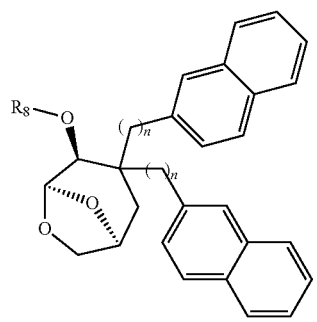

wherein $R^8$ is H, optionally substituted acyl, optionally substituted alkenylacyl, or a protecting group, and wherein n is an integer from 1 to 5.

More preferably, examples of compounds of formula (I") are represented below:

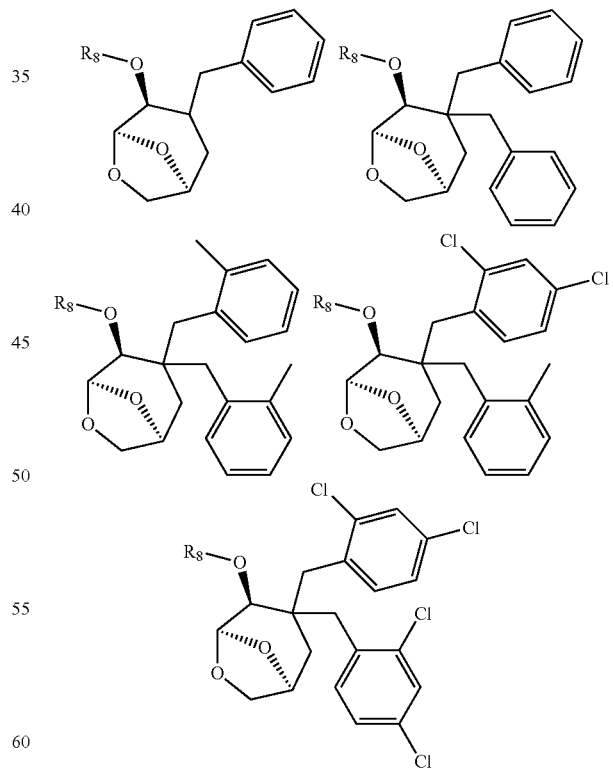

wherein $R^8$ is H, optionally substituted acyl, optionally substituted alkenylacyl, or a protecting group.

In a preferred embodiment, $R^8$ is H. In another preferred embodiment, $R^8$ is a protecting group.

In some embodiments, the enantiomerically enriched compound of formula (I''') is an enantiomerically pure compound of formula (I''').

In an embodiment, the present invention discloses enantiomerically enriched compound of formula (I''')

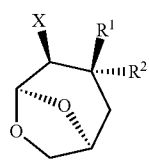
(I''')

or a salt thereof, wherein $R^1$, $R^2$ and X are as described above.

Accordingly, examples of compounds of formula (I''') are represented below:

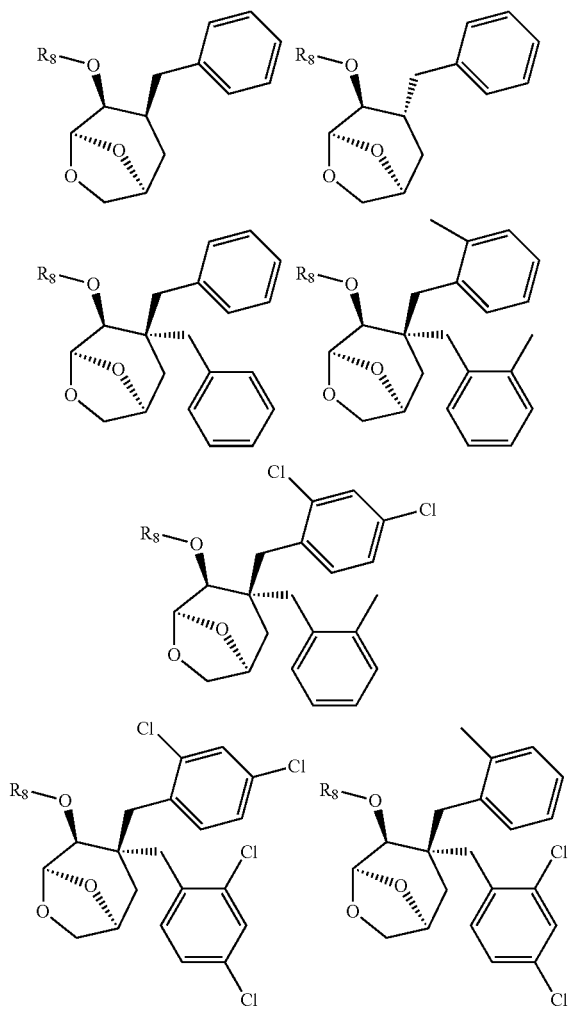

wherein $R^8$ is H, optionally substituted acyl, optionally substituted alkenylacyl, or a protecting group.

In an embodiment, the present invention discloses enantiomerically enriched compounds of formula (I''''):

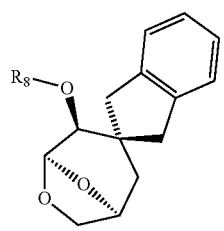
(I'''')

or a salt thereof, wherein $R^8$ is as described above. The chiral auxiliary depicted above may be considered to be a "tethered" chiral auxiliary, where the substituents at the carbon atom adjacent to the carbon-oxygen moiety form a spirocyclic compound. The present inventors have found that these tethered auxiliaries show greater stability when compared to the untethered analogues, as they do not undergo rearrangement at higher reaction temperatures. Other monocyclic or bicyclic groups are also contemplated by the present invention.

Without wishing to be bound by theory, it is believed that diastereoselectivity in a Diels-Alder reaction, for example, may be achieved through π-stacking interactions between the dienophile and the chiral auxiliary. Such π-stacking interactions require that a group, for example, an aryl group, be suitably positioned so as to interact with the alkene part of the dienophile such that the Diels-Alder reaction proceeds with diastereoselectivity. Accordingly, the enantiomerically enriched compound has at least one of $R^1$ or $R^2$ being optionally substituted aryl, optionally substituted heteroaryl, optionally substituted heteroarylalkyl or optionally substituted arylalkyl. Preferably, the enantiomerically enriched compound has at least one of $R^1$ or $R^2$ being optionally substituted arylalkyl and in a syn-relationship with respect to X. Preferably, the enantiomerically enriched compound has at least one of $R^1$ or $R^2$ being optionally substituted benzyl and in a syn-relationship with respect to X. Even more preferably, the enantiomerically enriched compound has at least one of $R^1$ or $R^2$ being optionally substituted benzyl and in a syn-relationship with respect to X, and X is in a syn-relationship with the methyleneoxy bridge. In cases where the chiral auxiliary is a compound of formula (I''''), i.e. where the chiral auxiliary is a tethered auxiliary, the syn relationship between the substituents $R^1$ or $R^2$ and X as described above is not applicable and instead, the spirocyclic nature of the tethered auxiliary provides the steric effects and subsequently imparts chirality on to the substrate.

In some embodiments, the enantiomerically enriched compound of formula (I''') is an enantiomerically pure compound of formula (I''').

In another aspect, the present invention provides a process for preparing a compound of formula (I), (I') or (I''). In this process a compound of formula (II):

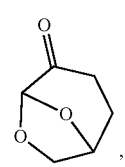
(II)

is reacted under suitable conditions to provide a compound of formula (III):

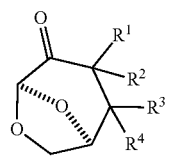

(III)

wherein the variables $R^1$, $R^2$, $R^3$ and $R^4$ are as defined herein. The compound of formula (III) is then reduced to provide a compound of formula (I), (I') or (I").

As defined above, the synthesis of the chiral auxiliaries described herein require a reduction step. Without wishing to be bound by theory, the present inventors believe that the stereochemical outcome of this reduction step is controlled by the methyleneoxy bridge of the substrate. During reduction, the approach of the nucleophile is from the face opposite the bridge, such that stereoselectivity is observed. This confers an advantage over other cyclohexanone-derived chiral auxiliaries, which usually yield mixtures upon reduction and subsequently require chromatographic separation. Furthermore, the bicyclic ring system of the present compounds often affords highly crystalline derivatives, such that the compounds may be prepared without any chromatographic purification steps.

In some embodiments, the reaction of a compound of formula (II) provides a compound of formula (IIIa):

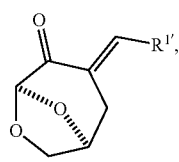

(IIIa)

wherein the group $R^{1'}$ and the adjacent carbon atom are equivalent to the group $R^1$, as defined above.

The process further comprises a step to reduce the alkene double bond to a single bond to provide a compound of formula (IIIb)

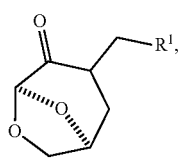

(IIIb)

wherein $R^1$ is as defined above.

In another embodiment, the process further comprises the step of epimerising the compound of formula (IIIb).

In another aspect, the present invention provides a compound of formula (I), (Ia), (I'), (I"), (I''') or (I'''') prepared according to a process as described herein.

In some embodiments, the present invention provides the use of an enantiomerically enriched compound of formula (I), (Ia), (I'), (I"), (I''') or (I'''') as a chiral auxiliary to control the stereochemical outcome of a cycloaddition or a conjugate addition reaction. In some embodiments, the use of an enantiomerically enriched compound of formula (I), (Ia), (I'), (I"), (I''') or (I'''') may be accompanied by the use of a suitable Lewis acid catalyst. In an embodiment, the cycloaddition reaction may be a Diels-Alder reaction.

A Diels-Alder reaction is a reaction between a conjugated diene and a substituted alkene (or a "dienophile"), such that a [4+2] cycloaddition reaction proceeds and forms a substituted cyclohexene through the formation of new sigma bonds. One skilled in the art would understand that the substitution pattern on the diene and the dienophile will influence the substitutions on the cyclohexene. Given the nature of the cycloaddition reaction, several stereocentres may be formed, with the nature of each stereocentre depending on the steric environment. Where a chiral auxiliary is attached to a substrate of the Diels-Alder reaction, the steric environment may be biased so as to favour the formation of a particular stereocentre over its opposite stereocentre. Where there are multiple stereocentres, this may lead to a particular diastereomer being formed.

The reactive parts of the substrates of a Diels-Alder reaction (i.e. the conjugated diene and the alkene or dienophile) may comprise carbon atoms only. The reaction of such substrates leads to the formation of cyclohexenes. Alternatively, the reactive parts of the substrates may comprise heteroatoms, for example, the dienophile may be a carbonyl compound or may be an imine, and comprise oxygen and nitrogen heteroatoms, respectively. Other heteroatoms, such as sulfur and phosphorus, may also be incorporated into the diene or the dienophile. Such a reaction may be known as a hetero Diels-Alder reaction.

The present inventors believe that the stereoselectivity of a reaction, for example, a Diels-Alder reaction, is influenced by the nature of the substituents at position alpha to the alcohol in the compounds of the present invention, where the compounds are used as a chiral auxiliary. For example, where the compounds comprise arylalkyl groups at the $R^1$ and $R^2$ positions, further substitution of these aryl groups to provide additional steric bulk provides better diastereoselectivity in the Diels-Alder reaction. Without wishing to be bound by theory, the inventors believe that the size, electronic and steric nature of the groups at the $R^1$ and $R^2$ positions in the present compounds may influence the stereochemical outcome of the reaction in which the compounds are employed as chiral auxiliaries. The present inventors also believe that the steric environment inherently provided by the bridged oxygen and the group represented by variable X may contribute to the stereoselectivity of the reaction.

The chiral auxiliary is incorporated into one of the substrates. The chiral auxiliary may have a reactive functional group, for example, an alcohol, amine or the like, that may react with a complementary functional group on the substrate, so as to form a covalent bond between the chiral auxiliary and the substrate. The resulting compound undergoes the desired reaction, after which the chiral auxiliary is removed under suitable conditions. For example, where a Diels-Alder reaction is intended, the chiral auxiliary may be bound to the dienophile, with the resulting compound subjected to the Diels-Alder reaction with a diene and the Diels-Alder product then treated so as to remove the chiral auxiliary. The chiral auxiliary for a particular Diels-Alder reaction, for example, may be chosen with consideration as to the nature of the substrates and the stereochemical requirements.

The chiral auxiliary may be incorporated into the desired substrate by reacting the alcohol of the chiral auxiliary with a suitable acid chloride. Alternatively, a coupling agent such as N,N'-dicyclohexylcarbodiimide may be used to couple the alcohol of the chiral auxiliary with a suitable carboxylic acid. The route by which the chiral auxiliary may be incorporated into the desired substrate will depend on the nature and reactivity of the chiral auxiliary and corresponding substrate to be attached.

Suitable Lewis acid catalysts for a Diels-Alder reaction may vary according to the diene and/or dienophile chosen. A Lewis acid may catalyse a Diels-Alder reaction by coordinating to the dienophile (or the complex of a dienophile and a chiral auxiliary) and increasing the reactivity of the substrate towards the diene. A Lewis acid catalyst may also influence the stereoselectivity and/or the regioselectivity of a particular transformation. Examples of a Lewis acid catalyst include, but are not limited to, $SnCl_4$, $AlCl_3$, $BF_3$ and $TiCl_4$.

Other reactions in which the compounds of the present invention may be used as a chiral auxiliary include other cycloaddition reactions and various conjugate addition reactions, for example, a Michael reaction with a thiol. Without wishing to be bound by theory, the present inventors consider that the stereochemical outcome of these other reactions may be influenced in a similar manner, where the compounds of the present invention are employed as chiral auxiliaries. The greater applicability of the chiral auxiliaries disclosed herein to different synthetic transformations means that more products with a defined stereochemistry may be accessed.

As described earlier, a substrate is reacted with a chiral auxiliary, before subsequent reaction under cycloaddition or conjugate addition conditions. The resulting addition product retains the chiral auxiliary. The present inventors have found that in some cases, the addition product-chiral auxiliary compound is more stable than the corresponding addition product without the chiral auxiliary. The addition product with the chiral auxiliary may be less prone to rearrangement (for example, in the presence of the Lewis acid used to catalyse a Diels-Alder reaction) and subsequent loss of stereochemistry. This may result in a product that has a better enantiomeric excess overall.

The present inventors have also found that the addition product-chiral auxiliary compound may undergo further reaction at a site distant to the chiral auxiliary, with the chiral auxiliary component tolerating a variety of conditions. For example, the product of a Michael reaction with a thiol produces a sulphide that may be oxidised to the corresponding sulfonyl compound.

The chiral auxiliary remains intact and the stereochemistry imparted by the chiral auxiliary in the earlier reaction is retained. Other reactions for specific functional groups may also be contemplated.

The addition product-chiral auxiliary compound may also be subjected to purification procedures, such as flash column chromatography on silica gel. This may allow for easier separation of the desired product from impurities, other materials or diastereomers, where present.

The inventors have also found that compounds of the present invention may be useful as chiral resolving agents. In another aspect, the present invention relates to the use of an enantiomerically enriched compound of the present invention as a resolving agent to separate an enantiomer of a compound from a mixture of its enantiomers.

The compound of the present invention, acting as a chiral resolving agent, may be added to a mixture of the enantiomers to be separated, so as to form different diastereomers. The chiral resolving agent may form a salt with the enantiomers to be separated, such as the salts formed are diastereomers of each other. Alternatively, the diastereomers formed may be a result of a covalent bond forming between each enantiomer and the chiral resolving agent. The diastereomers may be separated by means such as crystallisation or flash column chromatography, after which the resolving agent is removed by appropriate means.

Furthermore, depending on the substitution pattern the compounds of the present invention may be capable of tautomerism. Accordingly, all possible tautomers of a compound of the present invention fall within the scope and spirit of the invention.

Those skilled in the art will appreciate that the invention described herein may be susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features. For example, those skilled in the art will appreciate that the use of an enantiomerically enriched compound according to the present invention is not limited to control of the stereochemical outcome of a Diels-Alder reaction only.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Certain embodiments of the invention will now be described with reference to the following examples which are intended for the purpose of illustration only and are not intended to limit the scope of the generality hereinbefore described.

EXAMPLES

All reactions were carried out under $N_2$ unless indicated. Solvents were removed using a rotary evaporator with a bath temperature of 40° C. and pressure between 10 and 700 mbar. Non-volatile compounds were dried in vacuo. Solvents were distilled before use. (−)-Levoglucosenone and 6,8-dioxabicyclo[3.2.1]octan-4-one (Cyrene) were obtained from Circa, Melbourne, Australia (http://www.circagroup.com.au/levoglucosenone/). All other reagents were commercially available and were used as purchased. Except as otherwise indicated, reactions were magnetically stirred and monitored by NMR spectroscopy or thin layer chromatography (TLC) using silica plates (silica gel 60 F254). Visualisation occurred by fluorescence quenching under UV light and/or by staining with permanganate solution. Flash column chromatography was performed on silica-gel 60, using a moderate pressure applied via hand-pump. $^1$H NMR spectra were recorded at the indicated temperature on a 500 MHz Bruker Avance III spectrometer and the spectra were referenced to $CDCl_3$ (δ 7.26 ppm) or TMS (δ 0.00 ppm). $^{13}$C NMR spectra were recorded at 126 MHz and the residual solvent ($CDCl_3$, δ 77.16 ppm) was used as reference. NMR signals were assigned using COSY, NOESY, HSQC and HMBC experiments and the multiplicity was defined as follows: s=singlet, d=doublet, t=triplet, q=quartet, m=multiplet or unresolved, br=broad signal. IR spectra were recorded on a Perkin Elmer spectrometer and the signals are given in wavenumbers (cm$^{-1}$). Optical rotation was measured on a Rudolph Research Analytical Autopol 1 polarimeter operating at the sodium D line. Melting points were measured using open glass capillaries and are uncorrected. HRMS were recorded in positive ESI mode (source temperature 80° C., desolvation temperature 150° C., capillary 2.5 kV). The dr values were determined by NMR spectroscopy and GC-MS analysis. GC-MS analyses were performed using an Agilent Technologies 7890A GC-System coupled with an Agilent 5975C mass selective detector (triple-Axis detector) using a HP-5MS Agilent column (30 m×250 μm×0.25 μm). Oven temperature started at 50° C. for 5 min then heated at 20° C. per minute until 250° C. and then the temperature was held for 5 min. MS were acquired at −70 eV using a mass scan range of 30-400 m/z.

Example 1—Synthesis of a Mono-Substituted Chiral Auxiliary

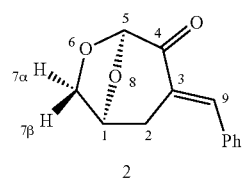

As per the literature procedure, a mixture of benzaldehyde (2.20 g, 1.2 equiv, 20.7 mmol) and TMG (2.20 mL, 1.0 equiv, 17.2 mmol) were heated to 100° C. Dihydrolevoglucosenone 1 (2.20 g, 1.76 mL, 1.0 equiv, 17.2 mmol) was added and the reaction mixture was stirred at 100° C. for 1 h then the mixture was directly applied to a column of silica and purified, eluting with EtOAc/hexanes 3:17. The resulting yellow solid was recrystallised with (i-Pr)$_2$O yielding enone 2 as yellow crystals (2.58 g, 69%); $^1$H NMR (500 MHz, CDCl$_3$): δ 7.72 (dd, J=2.8, 1.4 Hz, 1H, 9-H), 7.47-7.37 (m, 5H, Ar—H), 5.36 (s, 1H, 5-H), 4.89 (dd, J=5.3, 5.0 Hz, 1H, 1-H), 3.95 (ddd, J=7.3, 5.3, 1.4 Hz, 1H, 7-Hα), 3.82 (dd, J=7.3, 1.4 Hz, 1H, 7-Hβ), 3.36 (dddd, J=16.7, 5.0, 2.8, 1.4 Hz, 1H, 2-Hα), 2.91 (br d, J=16.7 Hz, 1H, 2-Hβ).

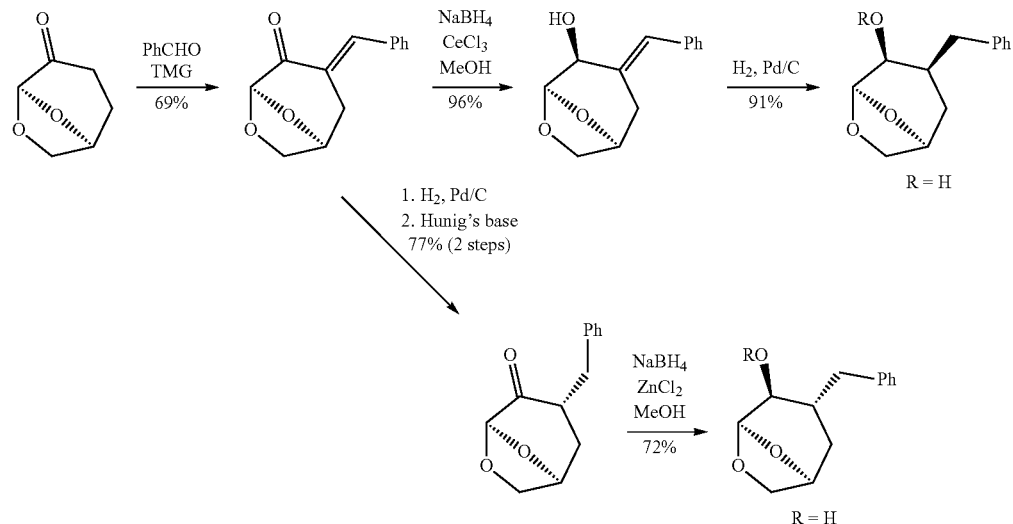

The mono-substituted derivatives shown below were prepared from an aldol reaction with cyrene and benzaldehyde. The subsequent reduction and epimerisation steps provided both the syn and anti products, with the desired product dependent on the order in which these steps are performed.

(1S,5R)-3-((E)-Benzylidene)-6,8-dioxabicyclo[3.2.1]octan-4-one (2)

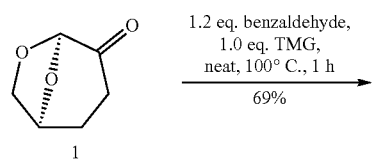

(1S,4S,5R)-3-((E)-Benzylidene)-6,8-dioxabicyclo[3.2.1]octan-4-ol (3)

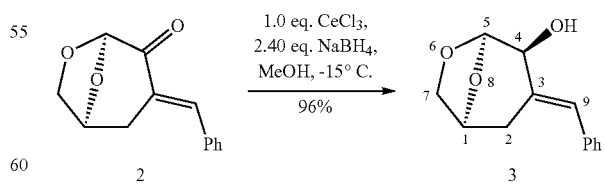

To a stirred solution of enone 2 (1.00 g, 1.0 equiv, 4.63 mmol) dissolved in MeOH (30 mL) cooled to 15° C. was added CeCl$_3$ (1.14 g, 1.0 equiv, 4.63 mmol). After stirring at 15° C. for 15 min, NaBH$_4$ (0.42 g, 2.4 equiv, 11.11 mmol) was added and the reaction mixture was stirred for 1 h. The mixture was carefully quenched with 0.5 M HCl (25 mL) and extracted with EtOAc (3×25 mL). The organic layers were combined, dried with MgSO₄, filtered and concentrated under reduced pressure. The residue was purified by recrystallisation using (i-Pr)₂O giving alcohol 3 as colourless crystals (980 mg, 96%); mp 107-108° C. (from (i-Pr)₂O); $[\alpha]_D^{25}$ −190 (c 1.2, CH₂Cl₂); ¹H NMR (500 MHz, CDCl₃): δ 7.36-7.33 (m, 2H, Ar—H), 7.25-7.20 (m, 3H, Ar—H), 6.97 (s, 1H, 9-H), 5.43 (d, J=2.2 Hz, 1H, 5-H), 4.59-4.56 (m, 1H, 1-H), 4.20 (ddt, J=11.6, 2.2, 1.1 Hz, 1H, 4-H), 3.76-3.73 (ddd, J=7.0, 5.4, 1.8 Hz, 1H, 7-Hα), 3.62 (dd, J=7.0, 1.1 Hz, 1H, 7-Hβ), 2.78-2.76 (dddd, J=15.2, 1.1, 0.8, 0.8 Hz, 1H, 2-Hα/β), 2.71-2.65 (m, 1H, 2-Hα/β), 1.89 (d, J=11.6 Hz, 1H, OH); ¹³C NMR (126 MHz, CDCl₃): δ 136.7, 136.0, 129.0, 128.5, 127.0, 126.9, 102.9, 73.5, 71.9, 68.6, 34.1. FT-IR (neat): 3422, 1415, 1186, 1086, 912 cm⁻¹; MS (EI) m/z: 218.1 ([M]⁺, trace), 172.1 (61), 171.1 (35), 157.1 (33), 143.1 (93), 141.1 (29), 131.1 (36), 129.1 (100), 128.1 (77), 115.1 (64), 91.1 (57).

(1S,3S,4S,5R)-3-Benzyl-6,8-dioxabicyclo[3.2.1]octan-4-ol (4)

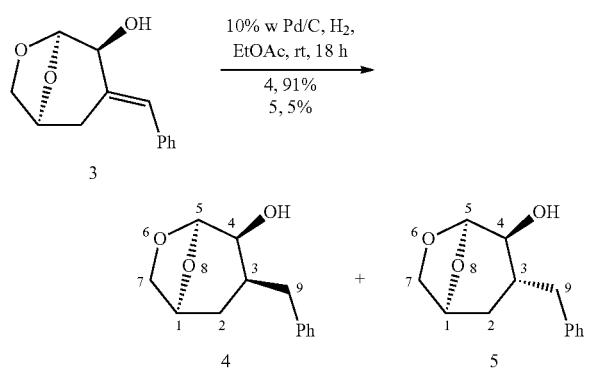

To a stirred solution of alcohol 3 (400 mg, 1.0 equiv, 1.83 mmol) in EtOAc was added 10% Pd/C (40 mg). A balloon of hydrogen was fitted and the reaction mixture was stirred under a H₂ atmosphere at 20° C. for 18 h. The mixture was filtered through celite, concentrated under reduced pressure and the residue purified by flash chromatography (MeOH/toluene 7:93). The product was further purified by recrystallisation from (i-Pr)₂O to give 4 as colourless crystals (366 mg, 91%) and 5 as colourless crystals (20 mg, 5%); 4: mp: 114-116° C. (from (i-Pr)₂O); $[\alpha]_D^{25}$ 62 (c 1.4, CH₂Cl₂); ¹H NMR (500 MHz, CDCl₃): δ 7.31-7.27 (m, 2H, Ar—H), 7.21-7.18 (m, 3H, Ar—H), 5.46 (d, J=4.1 Hz, 1H, 5-H), 4.48 (ddd, J=7.0, 4.7, 2.2 Hz, 1H, 1-H), 3.85 (ddd, J=9.5, 6.6, 4.1 Hz, 1H, 4-H), 3.81 (d, J=7.0 Hz, 1H, 7-Hβ), 3.72 (ddd, J=7.0, 4.7, 1.0 Hz, 1H, 7-Hα), 3.01 (dd, J=13.6, 6.6 Hz, 1H, 9-H), 2.55 (dd, J=13.6, 9.8 Hz, 1H, 9-H), 2.35 (d, J=9.5 Hz, 1H, OH), 2.19 (ddddd, J=9.8, 7.0, 6.9, 6.6, 6.6 Hz, 1H, 3-H), 1.99 (ddd J=14.2, 6.9 Hz, 1H, 2-H), 1.35 (ddd, J=14.2, 7.0, 2.1 Hz, 1H, 2-H); ¹³C NMR (126 MHz, CDCl₃): δ 140.9, 129.2, 128.5, 126.1, 100.5, 71.8, 70.5, 69.5, 35.4, 35.2, 30.2. FT-IR (neat): 3484, 2967, 2884, 1493, 1025, 900, 700 cm⁻¹; MS (EI) m/z: 220.2 ([M]⁺, trace), 156.1 (22), 134.1 (29), 133.1 (28), 118.1 (14), 117.1 (13), 105.1 (20), 92.1 (100), 91.1 (76), 78.1 (23), 65.1 (14).

(1S,3R,5R)-3-Benzyl-6,8-dioxabicyclo[3.2.1]octan-4-one (6)

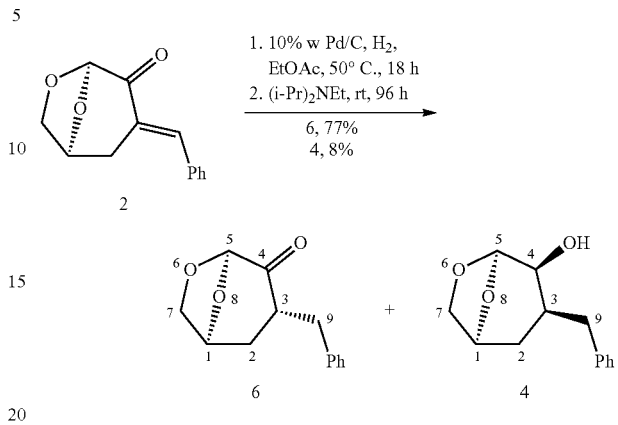

Using a modified literature procedure, enone 2 (1.4 g, 1.0 equiv, 6.48 mmol) was dissolved in EtOAc (20 mL) and 10% Pd/C (140 mg) was added. The reaction mixture was stirred at 50° C. for 18 h under a H₂ atmosphere and then filtered through celite. The volatiles were removed under reduced pressure and then the residue was dissolved in (i-Pr)₂EtN (25 mL) and the resulting mixture was stirred at 20° C. for 96 h. After concentration, the residue was purified by gradient flash chromatography (EtOAc/hexanes 3:17 to 1:1) to afford 6 as a yellowish oil (1.09 g, 77%) and 4 as colourless crystals (114 mg, 8%); 6: ¹H NMR (500 MHz, CDCl₃): δ 7.29-7.14 (m, 5H, Ar—H), 5.18 (s, 1H, 5-H), 4.67-4.65 (m, 1H, 1-H), 3.97 (d, J=7.4 Hz, 1H, 7-Hβ), 3.91-3.88 (m, 1H, 7-Hα), 3.36 (dd, J=14.1, 4.1 Hz, 1H, 9-H), 2.85 (dddd, J=11.4, 9.6, 8.2, 4.1 Hz, 1H, 3-H), 2.45 (dd, J=14.1, 9.6 Hz, 1H, 9-H), 1.99-1.89 (m, 2H, 2-H).

(1S,3R,4S,5R)-3-Benzyl-6,8-dioxabicyclo[3.2.1]octan-4-ol (5)

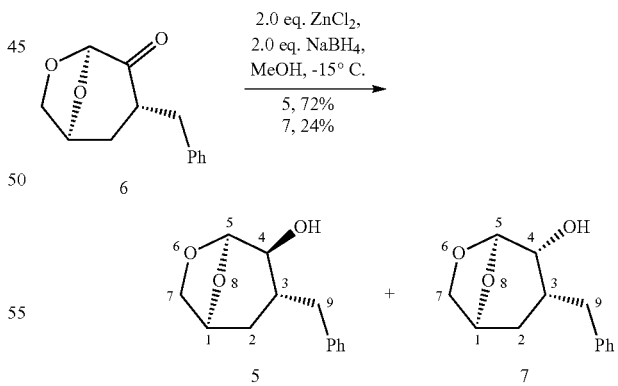

Ketone 6 (500 mg, 1.0 equiv, 2.3 mmol) was dissolved in MeOH (20 mL) and the solution was cooled to 15° C., then anhydrous ZnCl₂ (627 mg, 2.0 equiv, 4.6 mmol) was added. After 15 min of stirring at 15° C., NaBH₄ (210 mg, 2.4 equiv, 5.5 mmol) was added and the reaction mixture was stirred for 1 h at 15° C. then H₂O (10 mL) was added and the solution was extracted with EtOAc (3×15 mL). The organic layers were combined, dried with MgSO₄, filtered and concentrated under reduced pressure. The residue was further purified by flash chromatography (MeOH/toluene 7:93) to give 7 as a yellowish oil (121 mg, 24% which contained 3% of 5) and alcohol 5 which was further recrystallised from (i-Pr)$_2$O to give colourless crystals (364 mg, 72%); 7: mp 110-112° C. (from (i-Pr)$_2$O); [α]$_D^{25}$ −50 (c 1.2, CH$_2$Cl$_2$); $^1$H NMR (500 MHz, CDCl$_3$): δ 7.30-7.27 (m, 2H, Ar—H), 7.23-7.19 (m, 1H, Ar—H), 7.17-7.15 (m, 2H, Ar—H), 5.34 (s, 1H, 5-H), 4.48 (ddd, J=5.1, 3.5, 1.6 Hz, 1H, 1-H), 3.76-3.72 (m, 2H, 7-H), 3.35 (ddd, J=10.1, 9.8, 1.8 Hz, 1H, 4-H), 3.19 (dd, J=13.3, 3.9 Hz, 1H, 9-H), 2.40 (dd, J=13.3, 9.8 Hz, 1H, 9-H), 1.87-1.82 (m, 1H, 3-H), 1.69-1.49 (m, 3H, 2-H, OH); $^{13}$C NMR (126 MHz, CDCl$_3$): δ 139.7, 129.3, 128.6, 126.4, 102.4, 74.0, 73.6, 68.3, 39.8, 39.0, 33.7; FT-IR (neat): 3409, 2921, 1511, 1457, 1072, 974, 700 cm$^{-1}$; MS (EI) m/z: 220.2 ([M]$^+$, trace), 156.1 (22), 134.1 (60), 133.1 (88), 118.1 (22), 105.1 (37), 92.1 (100), 91.1 (95), 83.1 (25), 78.1 (41), 65.1 (23).

(1S,3R,4R,5R)-3-Benzyl-6,8-dioxabicyclo[3.2.1]octan-4-ol (7)

[α]$_D^{25}$ −72 (c 1.5, CH$_2$Cl$_2$); $^1$H NMR (500 MHz, CDCl$_3$): δ 7.29-7.26 (m, 2H, Ar—H), 7.21-7.17 (m, 3H, Ar—H), 5.38 (d, J=2.6 Hz, 1H, 5-H), 4.48 (ddd, J=5.0, 2.9, 2.9 Hz, 1H, 1-H), 3.83 (dd, J=7.0, 0.4 Hz, 1H, 7-Hβ), 3.75 (ddd, J=7.0, 5.0, 1.6 Hz, 1H, 7-Hα), 3.41 (ddd, J=10.6, 2.9, 2.9 Hz, 1H, 4-H), 2.78 (dd, J=13.4, 7.9 Hz, 1H, 9-H), 2.52 (dd, J=13.4, 7.5 Hz, 1H, 9-H), 2.18-2.10 (m, 1H, 3-H), 1.90 (d, J=10.6 Hz, 1H, OH), 1.72 (dddd, J=14.1, 13.0, 3.2, 1.5 Hz, 1H, 2-H), 1.47-1.42 (m, 1H, 2-H); $^{13}$C NMR (126 MHz, CDCl$_3$): δ 139.7, 129.2, 128.5, 126.2, 102.2, 73.0, 68.9, 67.4, 37.8, 34.1, 31.8; FT-IR (neat): 3415, 2911, 1504, 1458, 1072, 974, 702 cm$^{-1}$; MS (EI) m/z: 220.2 ([M]$^+$, trace), 156.1 (50), 134.1 (90), 133.1 (97), 115.1 (47), 105.1 (76), 92.1 (100), 91.1 (100), 83.1 (50), 78.1 (81), 65.1 (47).

Example 2—Synthesis of a Disubstituted Chiral Auxiliary

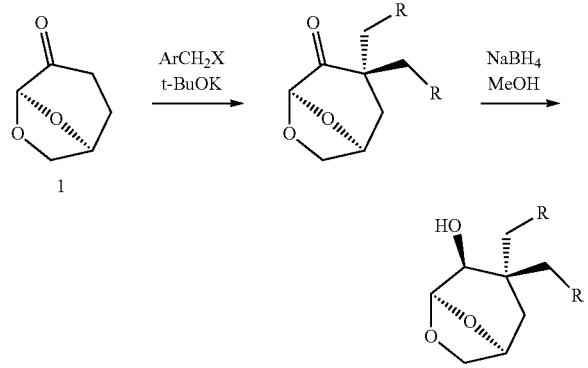

The di-substituted derivatives shown above were prepared by alkylation of cyrene 1 with a suitable halide in the presence of a base, with subsequent reduction to give the disubstituted alcohol.

(1S,5R)-3,3-Dibenzyl-6,8-dioxabicyclo[3.2.1]octan-4-one (8)

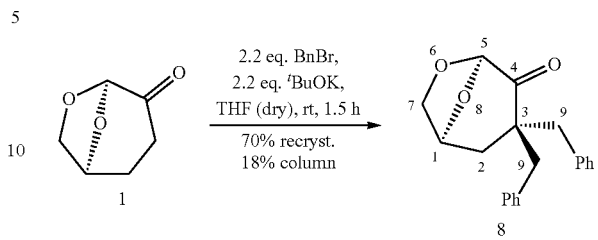

To a stirred solution of ketone 1 (5.0 g, 1.0 equiv, 39.0 mmol) and BnBr (14.7 g, 10.2 mL, 2.2 equiv, 85.9 mmol) in dry THF (50 mL) at 20° C. was added t-BuOK (10 g, 2.2 equiv, 85.9 mmol). The mixture was stirred until complete by TLC (1-3 h) then 1M HCl (50 mL) and EtOAc (200 mL) were added. The organic phase was separated and washed with sat. NaHCO$_3$ (150 mL) then brine (150 mL), dried over MgSO$_4$, filtered and concentrated under reduced pressure. If spontaneous crystallisation did not occur, residual benzyl bromide was removed using a high vacuum pump with warming. The residue was then dissolved in EtOAc/hexanes (1:4) mixture (50 mL) and allowed to crystallise for 24 h over which time some solvent evaporated to give a final volume of ~20 mL. The crystals were collected by vacuum filtration to give 8 as colourless crystals (8.40 g, 70%). Evaporation of the mother liquor and flash chromatography (EtOAc/hexanes 1:4) afforded an additional portion of 8 (2.20 g, 18%). $^1$H NMR (500 MHz, CDCl$_3$): δ 7.30-7.22 (m, 6H, Ar—H), 7.12-7.07 (m, 4H, Ar—H), 5.04 (s, 1H, 5-H), 4.53 (br dd, J=6.0, 5.5 Hz, 1H, 1-H), 3.53 (dd, J=6.9, 5.5 Hz, 1H, 7-Hα), 3.27 (d, J=13.3 Hz, 1H, 9-H), 3.26 (d, J=13.3 Hz, 1H, 9-H), 3.10 (d, J=7.20 Hz, 1H, 7-Hβ), 2.75 (d, J=13.3 Hz, 1H, 9-H), 2.58 (d, J=13.3 Hz, 1H, 9-H), 2.39 (dd, J=14.7, 6.0 Hz, 1H, 2-H), 1.75 (d, J=14.7 Hz, 1H, 2-H).

(1S,4S,5R)-3,3-Dibenzyl-6,8-dioxabicyclo[3.2.1]octan-4-ol (8)

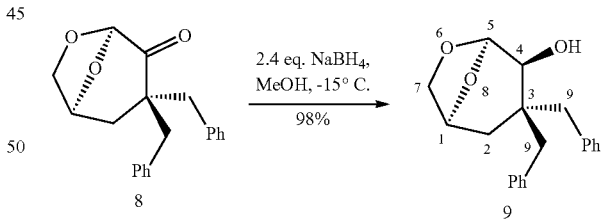

The ketone 8 (5.0 g, 1.0 equiv, 16.2 mmol) was dissolved in MeOH (120 mL) and the solution cooled to −15° C. Finely powdered NaBH$_4$ (1.47 g, 2.4 equiv, 39.0 mmol) was then added at a rate such that the temperature of the reaction did not exceed 0° C. After stirring for 2 h, the reaction was allowed to warm to ambient temperature and the reaction monitored by TLC. When no starting material remained, the reaction mixture was concentrated under reduced pressure and 1.0 M HCl (50 mL) was added. The aqueous phase was extracted with EtOAc (3×50 mL) ensuring that no product remained in the aqueous layer by TLC, then the organic layers were combined, dried with MgSO$_4$, filtered and concentrated under reduced pressure. The residue was recrystallised using an EtOAc/hexanes (1:4) mixture by slow evaporation to give 9 as colourless crystals (4.95 g, 98%); mp 126-127° C. (from (i-Pr)₂O); [α]$_D^{25}$ −43 (c 1.1, CH₂Cl₂); ¹H NMR (500 MHz, CDCl₃): δ 7.36-7.33 (m, 2H, Ar—H), 7.30-7.26 (m, 6H, Ar—H), 7.08-7.07 (m, 2H, Ar—H), 5.34 (d, J=2.0 Hz, 1H, 5-H), 4.43-4.41 (ddd, J=5.4, 2.8, 2.8, 1H, 1-H), 4.29 (d, J=7.5 Hz, 1H, 7-Hβ), 3.82 (dd, J=7.5, 5.4 Hz, 1H, 7-Hα), 3.71 (dd, J=10.0, 2.1 Hz, 1H, 4-H), 3.17 (d, J=13.9 Hz, 1H, 9-H), 3.02 (d, J=13.9 Hz, 1H, 9-H), 2.88 (d, J=13.4 Hz, 1H, 9-H), 2.38 (d, J=13.5 Hz, 1H, 9-H), 1.87-1.84 (m, 1H, OH), 1.74 (app br d, J=2.9 Hz, 2H, 2-H); ¹³C NMR (126 MHz, CDCl₃): δ 138.2, 137.7, 131.9, 131.6, 128.40, 128.38, 126.74, 126.67, 103.0, 73.7, 71.6, 68.1, 44.4, 41.4, 39.4, 31.1; FT-IR (neat): 3514, 2969, 1365, 1229, 897, 701 cm⁻¹; MS (ESI) m/z: 332.9 [M+Na]⁺.

(1S,4S,5R)-3,3-Bis(2-methylbenzyl)-6,8-dioxabicyclo[3.2.1]octan-4-ol (10)

gradient flash chromatography (EtOAc/hexanes 1:9 to 4:6) to give 10 as a colourless crystalline solid (390 mg, 30% overall yield); 10: mp 120-122° C.; [α]$_D^{25}$ −54 (c 1.0, CH₂Cl₂); ¹H NMR (500 MHz, CDCl₃): δ 7.25-7.16 (m, 4H, Ar—H), 7.10-7.06 (m, 3H, Ar—H), 6.97-6.96 (m, 1H, Ar—H), 5.37 (br s, 1H, 5-H), 4.43-4.41 (ddd, J=4.7, 4.7, 1.7 Hz, 1H, 1-H), 4.31 (d, J=7.6 Hz, 1H, 7-H), 3.81-3.79 (m, 1H, 7-H), 3.73-3.71 (m, 1H, 4-H), 3.30 (d, J=14.3 Hz, 1H, 9-H), 3.00 (d, J=14.3 Hz, 1H, 9-H), 2.87 (d, J=13.7 Hz, 1H, 9-H), 2.46 (s, 3H, CH₃), 2.28 (d, J=13.7 Hz, 1H, 9-H), 2.09 (dd, J=15.0, 1.4 Hz, 1H, 2-H), 2.05 (s, 3H, CH₃), 1.67 (dd, J=15.0, 4.1 Hz, 1H, 2-H); ¹³C NMR (126 MHz, CDCl₃): δ 138.6, 138.2, 136.8, 136.0, 132.4, 131.7, 131.2, 130.8, 126.7, 126.5, 125.51, 125.48, 103.0, 73.8, 71.8, 67.7, 43.7, 38.3, 33.9, 30.6, 21.3, 19.9; FT-IR (neat): 3510, 2959, 1640, 1340, 1229, 897, 704 cm⁻¹; MS (ESI) m/z: 361.1 [M+Na]⁺.

(1S,4S,5R)-3,3-Bis(2,4-dichlorobenzyl)-6,8-dioxabicyclo[3.2.1]octan-4-ol (13)

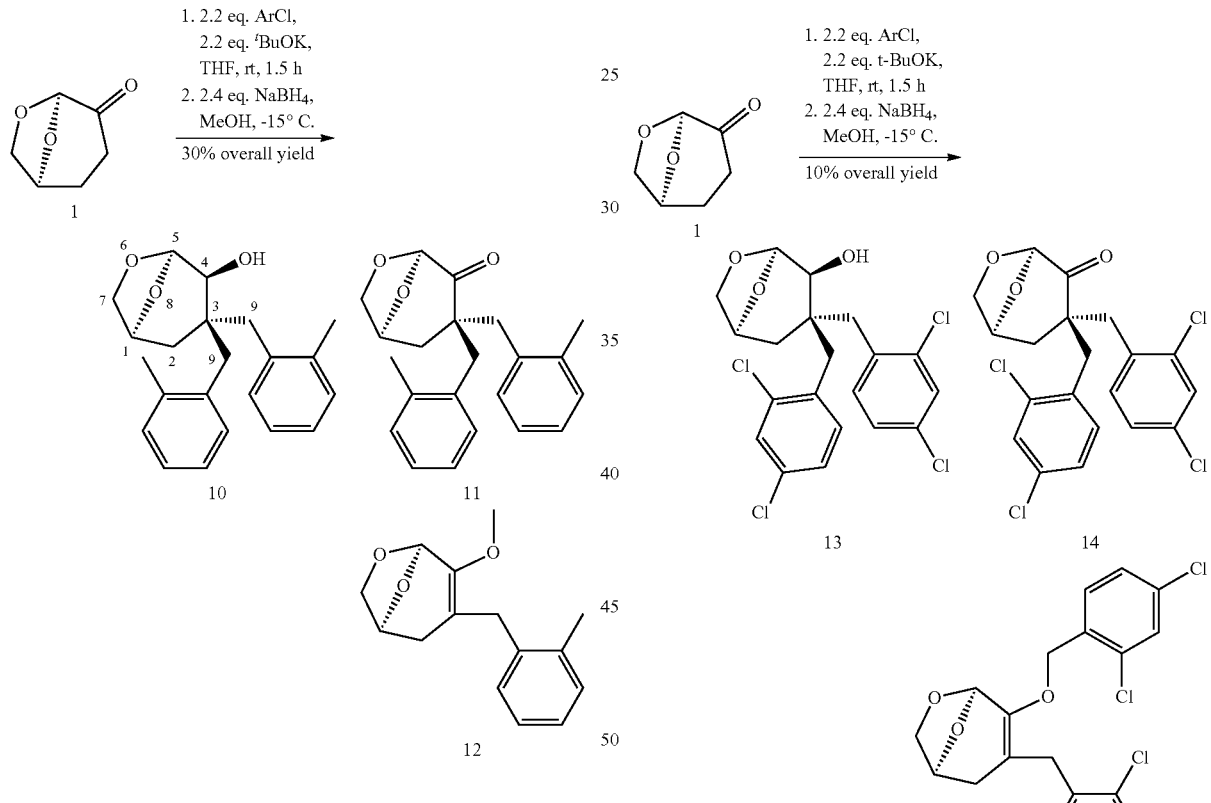

The reaction of 1 (500 mg, 1.0 equiv, 3.9 mmol), 2-methylbenzyl chloride (1.20 g, 2.2 equiv, 8.60 mmol) and t-BuOK (1.10 g, 2.2 equiv, 8.60 mmol) in THF (5 mL) as per the synthesis of 9 afforded ketone 11 (0.79 g, 54%) as a colourless wax containing 10% O-benzyl derivative 12. 11: ¹H NMR (500 MHz, CDCl₃): 7.10-6.95 (m, 8H, Ar—H), 5.13 (s, 1H, 5-H), 4.54-4.49 (m, 1H, 1-H), 3.50 (dd, J=6.7, 6.7 Hz, 1H, 7-Hα), 3.22 (d, J=14.8 Hz, 1H, 9-H), 3.11 (d, J=14.8 Hz, 1H, 9-H), 3.05 (d, J=6.7 Hz, 1H, 7-Hβ), 2.90 (d, J=14.8 Hz, 1H, 9-H), 2.71 (d, J=14.8 Hz, 1H, 9-H), 2.20 (dd, J=14.8, 7.8 Hz, 1H, 2-H), 2.17 (s, 3H, CH₃), 2.13 (s, 3H, CH₃), 1.51 (d, J=14.8 Hz, 1H, 2-H). Ketone 11 thus obtained (0.79 g, purity ~90%, 1.0 equiv, 2.10 mmol) in methanol (20 mL) was treated as per 8 using NaBH₄ (210 mg, 2.4 equiv, 5.6 mmol). After workup, the crude alcohol was purified by The reaction of 1 (500 mg, 1.0 equiv, 3.9 mmol), 2,4-dichlorobenzyl chloride (2.05 g, 2.2 equiv, 8.59 mmol) and t-BuOK (1.10 g, 2.2 equiv, 8.60 mmol) in THF (5 mL) as per the synthesis of 8 afforded a mixture of 14 and 15 as a colourless wax (645 mg, 2:1 14/15, adjusted yield of 14=24%). 14: ¹H-NMR (500 MHz, CDCl₃): δ 7.47-7.32 (m, 3H, Ar—H), 7.19-6.92 (m, 3H, Ar—H), 5.17 (s, 1H, 5-H), 4.65 (br s, 1H, 1-H), 4.64 (br d, 1H, 7-H), 3.65 (dd, J=5.9, 5.9 Hz, 1H, 7-H), 3.34 (d, J=14.0 Hz, 1H, 9-H), 3.29 (d, J=14.0 Hz, 1H, 9-H), 3.19 (d, J=14.0 Hz, 1H, 9-H), 3.14 (d, J=14.0 Hz, 1H, 9-H), 2.37 (dd, J=15.1, 6.8 Hz, 1H, 2-H), 1.79 (d, J=15.1 Hz, 2-H). Ketone 14 thus obtained (645 mg (66% pure) was dissolved in MeOH (10 mL) was treated as per 8 using NaBH$_4$ (130 mg, 2.4 equiv, 3.47 mmol). After workup, the crude alcohol was purified by gradient flash chromatography (EtOAc/hexanes 1:9 to 4:6) to give 13 as a colourless crystalline solid (270 mg, 40%, 10% overall yield); 13: $[\alpha]_D^{25}$ −79 (c 1.2, CH$_2$Cl$_2$); $^1$H NMR (500 MHz, CDCl$_3$): δ 7.43-7.41 (m, 1H, Ar—H), 7.37-7.34 (m, 2H, Ar—H), 7.24-7.21 (m, 1H, Ar—H), 7.18-7.15 (m, 1H, Ar—H), 7.02-6.99 (m, 1H, Ar—H), 5.37 (d, J=1.7 Hz, 1H, 5-H), 4.45 (ddd, J=4.3, 4.3, 1.5 Hz, 1H, 1-H), 4.26 (d, J=7.5 Hz, 1H, 7-Hβ), 3.79 (dd, J=7.5, 4.3 Hz, 1H, 7-H), 3.68 (d, J=14.3 Hz, 1H, 9-H), 3.60 (dd, J=8.3, 1.7 Hz, 1H, 4-H), 3.12 (d, J=14.3 Hz, 1H, 9-H), 2.97 (d, J=14.3 Hz, 1H, 9-H), 2.35 (d, J=14.3 Hz, 1H, 9-H), 2.18 (d, J=8.3 Hz, 1H, OH), 2.00 (dd, J=15.3, 1.6 Hz, 1H, 2-H), 1.76 (dd, J=15.3, 4.3 Hz, 1H, 2-H); $^{13}$C NMR (126 MHz, CDCl$_3$): δ 136.9, 136.5, 135.3, 134.5, 134.1, 134.0, 133.4, 133.0, 130.0, 129.7, 127.0, 126.9, 102.8, 73.5, 71.2, 67.7, 43.5, 38.4, 35.3, 32.9; FT-IR (neat): 3449, 2956, 1733, 1489, 1048, 733 cm$^{-1}$; MS (ESI) m/z: 449.3 [M+H]$^+$.

Example 3—Synthesis of a Tethered Chiral Auxiliary

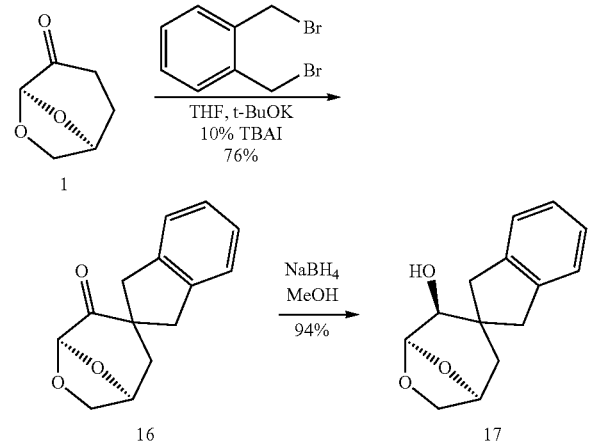

The tethered derivative 17 was prepared from an alkylation reaction with cyrene 1 and dibromoxylene and subsequent reduction of carbonyl group to the alcohol.

(1S,5R)-1',3'-Dihydro-6,8-dioxaspiro[bicyclo[3.2.1]octane-3,2'-inden]-4-one (16)

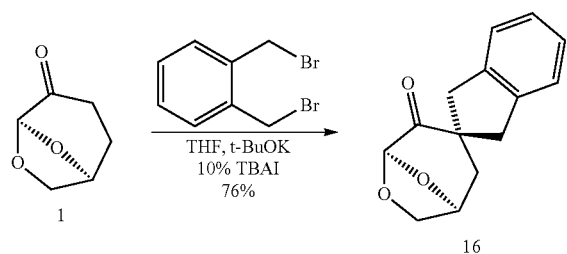

Dibromoxylene (25.0 g, 1.2 equiv, 105 mmol) was dissolved in dry THF (100 mL) and the reaction mixture was cooled down to 0° C. To this solution was added TBAI (3.2 g, 0.1 equiv, 8.7 mmol), t-BuOK (24.3 g, 2.5 equiv, 218 mmol) followed by the dropwise addition of diluted 1 (11.2 g, 1.0 equiv, 87 mmol) in THF (100 mL). After stirring for 4 h at 0° C., 1.0 M HCl (250 mL) and EtOAc (100 mL) were added. The aqueous layer was extracted additionally with EtOAc (2×50 mL). The organic layers were combined, dried over MgSO$_4$ and concentrated. The residue was further purified by flash column chromatography on silica (200 g) with toluene (750 mL) to give 16 (15.2 g, 76%) as an orange wax. $[\alpha]_D^{25}$ −174 (c 1.0, CH$_2$Cl$_2$); $^1$H NMR (500 MHz, CDCl$_3$): δ 7.21-7.10 (m, 4H), 5.25 (s, 1H), 4.75 (dd, J=4.8, 4.8 Hz, 1H), 4.18 (d, J=7.0 Hz, 1H), 3.91 (ddd, J=7.0, 4.8, 1.6 Hz, 1H), 3.74 (d, J=15.9 Hz, 1H), 3.50 (d, J=16.2 Hz, 1H), 3.18 (d, J=15.9 Hz, 1H), 2.70 (d, J=16.2 Hz, 1H), 2.37 (ddd, J=14.6, 4.8, 1.6 Hz, 1H), 2.18 (d, J=14.6 Hz, 1H); $^{13}$C NMR (125 MHz, CDCl$_3$): δ 203.1, 141.0, 139.9, 127.2, 126.9, 124.5, 124.4, 101.5, 73.9, 68.0, 51.7, 46.7, 45.1, 42.8; FT-IR (neat): ν=2914, 1725, 1485, 1118, 1098, 747 cm$^{-1}$; MS (ESI) m/z: 253.0 [M+Na]$^+$; ESI-HRMS Calcd for [M+Na]$^+$ C$_{14}$H$_{14}$O$_3$Na: 253.0841; found: 253.0832.

(1S,4S,5R)-1',3'-Dihydro-6,8-dioxaspiro[bicyclo[3.2.1]octane-3,2'-inden]-4-ol (17)

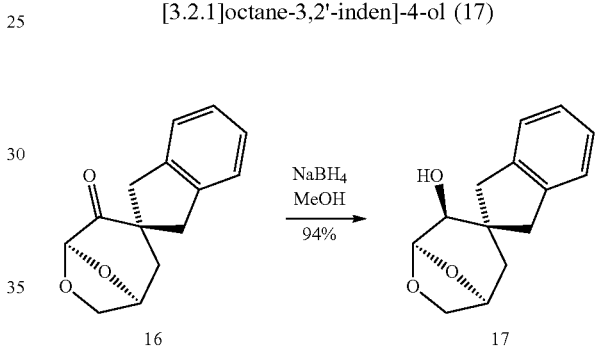

A solution of 16 (15.2 g, 1.0 equiv, 66 mmol) in CH$_2$Cl$_2$ (100 mL) and MeOH (200 mL) was cooled down to −15° C. and NaBH$_4$ was added portion wise (1.7 g, 0.7 equiv, 46.2 mmol). After stirring at −15° C. for 3 h the reaction mixture was concentrated under reduced pressure and CH$_2$Cl$_2$ (250 mL) and 1.0 M HCl (250 mL) were added. Following separation, the aqueous layer was extracted with CH$_2$Cl$_2$ (2×100 mL) and the combined organic layers were dried over MgSO$_4$ and concentrated. The residue was recrystallized with EtOAc/hexanes to give 17 (14.4 g, 94%) as yellowish crystals. mp 92-94° C.; $[\alpha]_D^{25}$ −164 (c 1.0, CH$_2$Cl$_2$); $^1$H NMR (500 MHz, CDCl$_3$): δ 7.20-7.09 (m, 4H), 5.38 (d, J=1.6 Hz, 1H), 4.53 (ddd, J=4.8, 4.3, 1.4 Hz, 1H), 4.10 (d, J=7.3 Hz, 1H), 3.78 (ddd, J=7.3, 4.8, 1.4 Hz, 1H), 3.69 (dd, J=7.6, 1.6 Hz, 1H), 3.64 (d, J=16.3 Hz, 1H), 3.18 (d, J=16.3 Hz, 1H), 2.85 (d, J=16.3 Hz, 1H), 2.84 (d, J=16.3 Hz, 1H), 2.05 (ddd, J=14.6, 4.3, 1.4 Hz, 1H), 1.92 (dd, J=14.6, 1.4 Hz, 1H), 1.67 (d, J=7.6 Hz, OH); $^{13}$C NMR (125 MHz, CDCl$_3$): δ 143.1, 140.9, 126.7, 126.6, 124.4, 124.2, 102.5, 76.5, 74.0, 67.9, 48.7, 46.8, 40.7, 39.8; FT-IR (neat): ν=2924, 1711, 1363, 1220, 1078, 924 cm$^{-1}$; MS (ESI) m/z: 255.1 [M+Na]$^+$; ESI-HRMS Calcd for [M+H]$^+$ C$_{14}$H$_{17}$O$_3$: 233.1178; found: 233.1169.

Example 4—Acylation of a Chiral Auxiliary with a Dienophile

The chiral auxiliary may be functionalised at the hydroxyl group to provide a dienophile or another reactive functional group. The manner in which the functional group is installed depends on the nature of the functional group, the coupling partner, the reactivity of these groups and tolerance of the substrate overall to the required reaction conditions.

The examples below demonstrate several methods in which a chiral auxiliary may be acylated in order to provide a compound that can undergo further reaction.

a) Acylation with an Acid Chloride

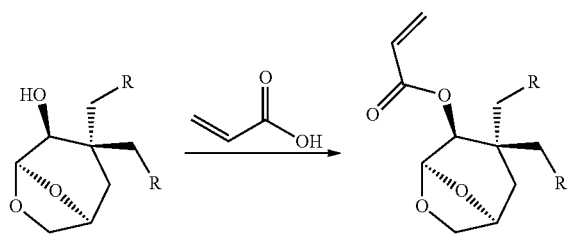

The desired dienophile for a Diels-Alder reaction or similar was selected (for example, acrylic acid) and the chiral auxiliary installed on the relevant acrylate to produce the corresponding ester. The acrylic acid, as shown in this example, may be freshly prepared from a reaction of acryloyl chloride in the presence of pyridine and triethylamine.

b) Acylation with N,N'-Dicyclohexylcarbodiimide and Carboxylic Acid

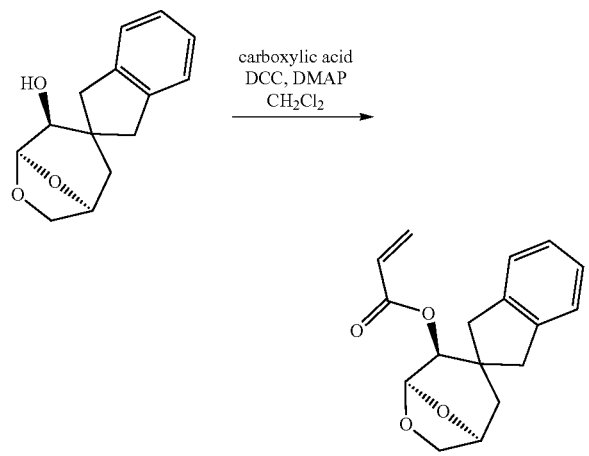

The desired dienophile for a Diels-Alder reaction can be prepared in a coupling reaction with a carboxylic acid mediated by N,N'-dicyclohexylcarbodiimide (DCC).

c) Acylation to Provide a Trifluoromethyl-Substituted Dienophile

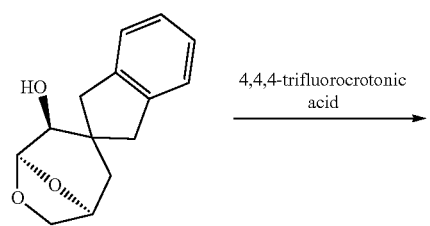

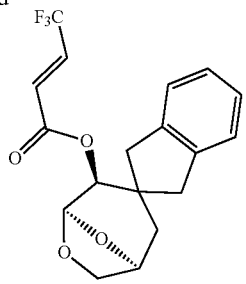

A trifluoromethyl-substituted dienophile bound to the chiral auxiliary can be produced from a reaction with the hydroxy group of the chiral auxiliary with 4,4,4-trifluorocrotonic acid.

(1S,4S,5R)-6,8-Dioxabicyclo[3.2.1]oct-2-en-4-yl acrylate (19)

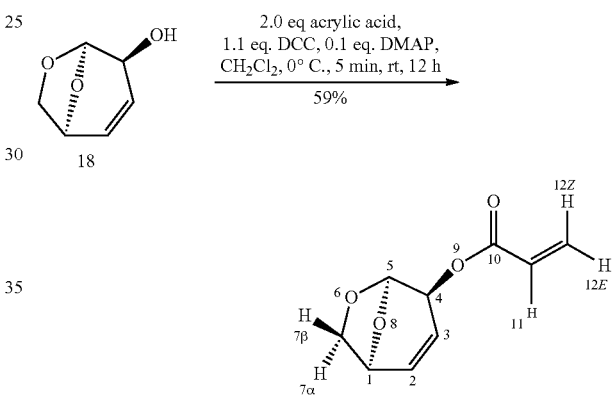

Following a literature procedure, acrylic acid (141 mg, 2.0 equiv, 1.56 mmol) and alcohol 18 (100 mg, 1.0 equiv, 0.78 mmol) derived from levoglucosenone in 91% yield was dissolved in dry DCM (8 mL) and 4-dimethylaminopyridine (DMAP) (19 mg, 0.1 equiv 0.16 mmol) was added. The solution was cooled to 0° C. and then dicyclohexylcarbodiimide (DCC) (176 mg, 1.1 equiv, 0.86 mmol) was added. After stirring for 5 min at 0° C., the reaction was allowed to warm to room temperature and stirred for another 12 h. The mixture was filtered, concentrated under reduced pressure and the residue purified by flash chromatography (EtOAc/hexanes 2:3) to give 19 as a colourless wax (85 mg, 59%); $[\alpha]_D^{25}$ −143 (c 1.0, $CH_2Cl_2$); $^1H$ NMR (500 MHz, $CDCl_3$): δ 6.48 (br d, J=17.8 Hz, 1H, 12-HZ), 6.23-6.17 (m, 2H, 11-H, 2-H), 5.88 (br d, J=10.4 Hz, 1H, 12-HE), 5.67-5.59 (m, 2H, 3-H, 5-H), 5.59 (d, J=1.0 Hz, 1H, 4-H), 4.71-4.70 (m, 1H, 1-H), 3.99 (dd, J=6.6, 1.3 Hz, 1H, 7-Hβ), 3.82-3.80 (m, 1H, 7-Hα); $^{13}C$ NMR (126 MHz, $CDCl_3$): δ 166.1, 132.7, 131.9, 128.0, 124.9, 99.3, 71.9, 71.6, 71.5; FT-IR (neat): 2950, 1735, 1360, 1220, 890, 715 $cm^{-1}$; MS (ESI) m/z: 195.1 $[M+Na]^+$.

(1S,3R,4S,5R)-3-Benzyl-6,8-dioxabicyclo[3.2.1]octan-4-yl acrylate (20)

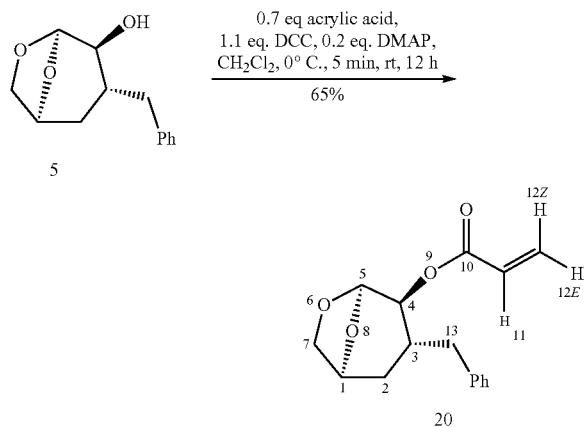

The reaction of alcohol 5 (100 mg, 1.0 equiv, 0.45 mmol) with DCC (103 mg, 1.1 equiv, 0.50 mmol), DMAP (11 mg, 0.2 equiv, 0.09 mmol) and acrylic acid (23 mg, 0.7 equiv, 0.32 mmol) as per compound 19 afforded ester 20 as a colourless wax (76 mg, 0.28 mmol, 88%); $[\alpha]_D^{25}$ −116 (c 1.0, CH$_2$Cl$_2$); $^1$H NMR (500 MHz, CDCl$_3$): δ 7.28-7.26 (m, 2H, Ar—H), 7.20-7.17 (m, 1H, Ar—H), 7.17-7.11 (m, 2H, Ar—H), 6.43 (dd, J=17.3, 1.3 Hz, 1H, 12-HZ), 6.13 (dd, J=17.3, 10.4 Hz, 1H, 11-H), 5.85 (dd, J=10.4, 1.3 Hz, 1H, 12-HE), 5.43 (d, J=1.4 Hz, 1H, 5-H), 4.65 (dd, J=9.7, 1.6 Hz, 1H, 4-H), 4.46-4.42 (m, 1H, 1-H), 3.75 (br d, J=6.9 Hz, 1H, 7-Hβ), 3.69 (ddd, J=6.9, 5.1, 1.2 Hz, 1H, 7-Hα), 2.81 (dd, J=13.0, 4.0 Hz, 1H, 13-H), 2.40 (dd, J=13.0, 8.0 Hz, 1H, 13-H), 2.35-2.26 (m, 1H, 3-H), 1.68-1.57 (m, 2H, 2-H); $^{13}$C NMR (126 MHz, CDCl$_3$): δ 166.0, 139.1, 131.7, 129.2, 128.6, 128.1, 126.4, 99.8, 75.9, 73.5, 68.6, 39.0, 35.2, 34.0; FT-IR (neat): 2950, 1735, 1360, 1220, 890, 715 cm$^{-1}$; MS (ESI) m/z: 297.1 [M+Na]$^+$.

(1S,3S,4S,5R)-3-Benzyl-6,8-dioxabicyclo[3.2.1]octan-4-yl acrylate (21)

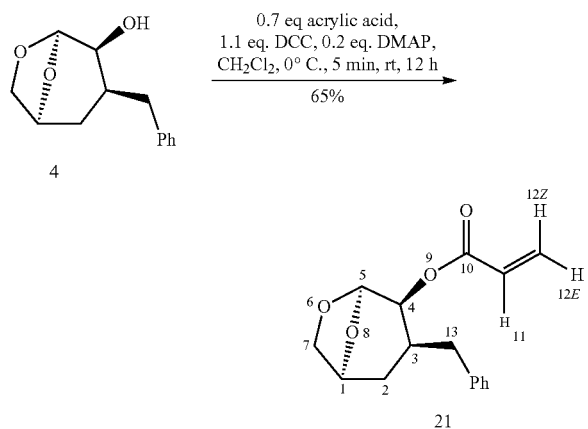

The reaction of alcohol 4 (50 mg, 1.0 equiv, 0.23 mmol) with acrylic acid (18 mg, 1.1 equiv, 0.25 mmol), DMAP (6 mg, 0.2 equiv, 0.05 mmol) and DCC (50 mg, 1.1 equiv 0.25 mmol) in DCM (2.3 mL) as for the synthesis of 19 afforded 21 as a colourless wax (40 mg, 65%); $[\alpha]_D^{25}$ −105 (c 1.0, CH$_2$Cl$_2$); $^1$H NMR (500 MHz, CDCl$_3$): δ 7.29-7.26 (m, 2H, Ar—H), 7.20-7.19 (m, 1H, Ar—H), 7.15-7.08 (m, 2H, Ar—H), 6.47 (dd, J=17.3, 1.4 Hz, 1H, 12-HZ), 6.19 (dd, J=17.3, 10.4 Hz, 1H, 11-H), 5.88 (dd, J=10.4, 1.4 Hz, 1H, 12-HE), 5.52 (d, J=2.4 Hz, 1H, 5-H), 4.97 (dd, J=6.8, 2.4 Hz, 1H, 4-H), 4.49 (ddd, J=5.2, 4.4, 1.3 Hz, 1H, 1-H), 4.01 (dd, J=7.2, 1.3 Hz, 1H, 7-Hβ), 3.82 (dd, J=7.2, 5.2, 1.6 Hz, 1H, 7-Hα), 2.97 (dd, J=14.1, 5.7 Hz, 1H, 13-H), 2.76 (dd, J=14.1, 11.1 Hz, 1H, 13-H), 2.68-2.61 (m, 1H, 3-H), 2.02 (ddd, J=14.7, 7.3, 4.4 Hz, 1H, 2-H), 1.55 (dd, J=14.7, 3.2 Hz, 1H, 2-H); $^{13}$C NMR (126 MHz, CDCl$_3$): δ 165.7, 140.6, 131.7, 129.1, 128.7, 128.1, 126.3, 100.0, 73.0, 72.8, 69.4, 35.4, 34.1, 30.0; FT-IR (neat): 2950, 1735, 1360, 1220, 890, 715 cm$^{-1}$; MS (ESI) m/z: 297.0 [M+Na]$^+$.

(1S,4S,5R)-3,3-Dibenzyl-6,8-dioxabicyclo[3.2.1]octan-4-yl acrylate (22)

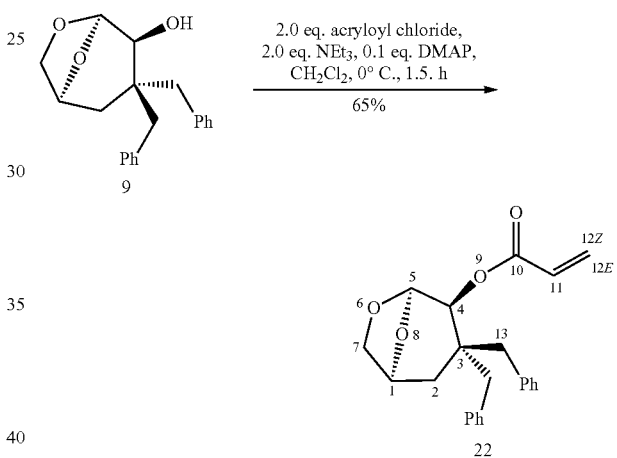

Alcohol 9 (500 mg, 1.0 equiv, 1.61 mmol) was dried by coevaporation with toluene then dissolved in DCM (15 mL) and NEt$_3$ (325 mg, 2.0 equiv, 3.23 mmol) and DMAP (39 mg, 0.2 equiv, 0.32 mmol) were added. The mixture was cooled to 0° C. and freshly distilled acryloyl chloride (290 mg, 2.0 equiv, 3.22 mmol) was added. The mixture was kept at 0° C. for 1.5 h then quenched by the addition of sat. NaHCO$_3$ (15 mL) and stirred for a further 30 min. The organic layer was separated and the aqueous layer extracted with ethyl acetate (2×30 mL), then the combined organic layers dried with MgSO$_4$, filtered and concentrated under reduced pressure. The residue was recrystallised from hot (i-Pr)$_2$O to give 22 as colourless crystals (380 mg, 65%); mp 89-91° C.; $[\alpha]_D^{25}$ −126 (c 0.9, CH$_2$Cl$_2$); $^1$H NMR (500 MHz, CDCl$_3$): δ 7.39-7.36 (m, 2H, Ar—H), 7.31 (m, 2H, Ar—H), 7.27-7.23 (m, 4H, Ar—H), 7.03 (m, 2H, Ar—H), 6.54 (d, J=17.3 Hz, 1H, 12-HZ), 6.26 (dd, J=17.3, 10.4 Hz, 1H, 11-H), 5.95 (d, J=10.4 Hz, 1H, 12-HE), 5.47 (d, J=1.8 Hz, 1H, 5-H), 5.03 (d, J=1.8 Hz, 1H, 4-H), 4.45 (br s, 1H, 1-H), 4.37 (d, J=7.4 Hz, 1H, 7-Hβ), 3.86-3.83 (dd, J=7.4, 4.8 Hz, 1H, 7-Hα), 3.47 (d, J=14.6 Hz, 1H, 13-H), 3.14 (d, J=14.6 Hz, 1H, 13-H), 2.71 (d, J=13.6 Hz, 1H, 13-H), 2.50 (d, J=13.6 Hz, 1H, 13-H), 1.83-1.81 (m, 2H, 2-H); $^{13}$C NMR (126 MHz, CDCl$_3$): δ 165.7, 138.2, 136.8, 131.9, 131.8, 131.5, 128.34, 128.33, 128.29, 126.8, 126.6, 100.0, 73.5, 73.4, 68.0, 44.2, 40.6, 40.1, 31.5; FT-IR (neat): 2961, 1742, 1360, 1229, 895, 710 cm$^{-1}$; MS (ESI) m/z: 387.1 [M+Na]$^+$.

(1S,4S,5R)-3,3-Bis(2-methylbenzyl)-6,8-dioxabicyclo[3.2.1]octan-4-yl acrylate (23)

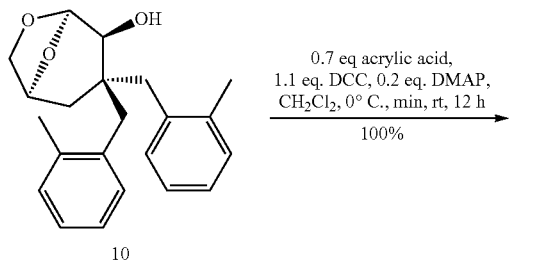

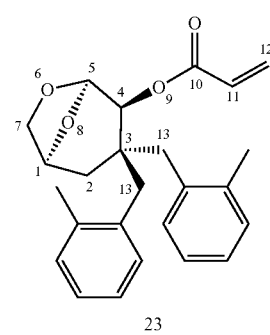

The reaction of 10 (50 mg, 1.0 equiv, 0.16 mmol), DMAP (4 mg, 0.2 equiv, 0.03 mmol), DCC (34 mg, 1.1 equiv, 0.17 mmol) and acrylic acid (8 mg, 0.7 equiv, 0.10 mmol) as per compound 19 afforded 23 as a colourless wax (38 mg, 0.10 mmol, 100%); [α]$_D^{25}$ −137 (c 1.3, CH$_2$Cl$_2$); $^1$H NMR (500 MHz, CDCl$_3$): δ 7.24-7.05 (m, 8H, Ar—H), 6.60 (dd, J=17.3, 1.3 Hz, 1H, 12-HZ), 6.33 (dd, J=17.3, 10.4 Hz, 1H, 11-H), 5.99 (dd, J=10.4, 1.3 Hz, 1H, 12-HE), 5.51 (d, J=1.7 Hz, 1H, 5-H), 5.18 (d, J=1.7 Hz, 1H, 4-H), 4.43 (ddd, J=4.8, 4.5, 1.5 Hz, 1H, 1-H), 4.36 (d, J=7.5 Hz, 1H, 7-Hβ), 3.81 (dd, J=7.5, 4.8, 1H, 7-Hα), 3.49 (d, J=14.9 Hz, 1H, 13-H), 3.24 (d, J=14.9 Hz, 1H, 13-H), 2.44-2.34 (m, 2H, 13-H), 2.40 (s, 3H, CH$_3$), 2.17 (br d, J=14.9 Hz, 1H, 2-H), 1.77 (s, 3H, CH$_3$), 1.59 (dd, J=14.9, 4.5 Hz, 1H, 2-H); $^{13}$C NMR (126 MHz, CDCl$_3$): δ 165.8, 138.4, 137.7, 136.9, 135.3, 134.7, 131.9, 131.5, 131.0, 130.5, 128.2, 126.7, 126.4, 126.0, 125.5, 100.1, 73.7, 73.5, 67.8, 43.0, 37.3, 34.4, 30.9, 21.0, 19.6; FT-IR (neat): 2967, 1736, 1369, 1220, 890, 715 cm$^{-1}$; MS (ESI) m/z: 393.2 [M+H]$^+$, 415.1 [M+Na]$^+$.

(1S,4S,5R)-3,3-Bis(2,4-dichlorobenzyl)-6,8-dioxabicyclo[3.2.1]octan-4-yl acrylate (24)

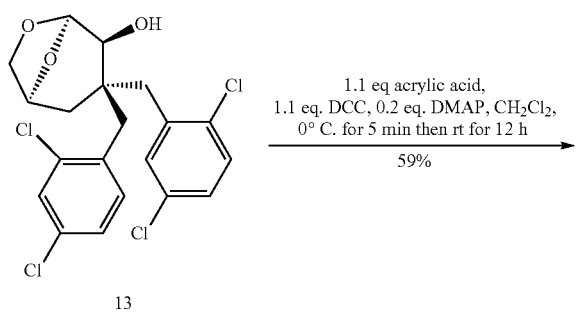

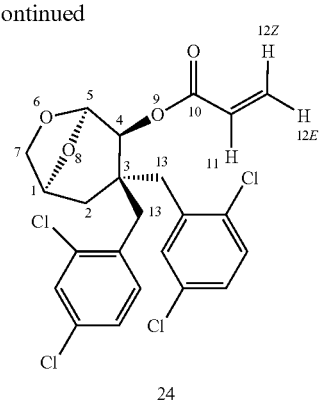

The reaction of 13 (50 mg, 1.0 equiv, 0.11 mmol), acrylic acid (11 mg, 1.0 equiv, 0.11 mmol), DCC (25 mg, 1.1 equiv, 0.12 mmol) and DMAP (3 mg, 0.2 equiv, 0.02 mmol) as per compound 19 afforded 24 as a colourless wax (33 mg, 59%); [α]$_D^{25}$ −121 (c 1.0, CH$_2$Cl$_2$); $^1$H NMR (500 MHz, CDCl$_3$): δ 7.47 (d, J=2.1 Hz, 1H, Ar—H), 7.36-7.34 (m, 2H, Ar—H), 7.27-7.26 (m, 1H, Ar—H), 7.22-7.21 (m, 2H, Ar—H), 6.63 (d, J=17.3 Hz, 1H, 12-HZ), 6.35 (dd, J=17.3, 10.4 Hz, 1H, 11-H), 6.03 (d, J=10.4 Hz, 1H, 12-HE), 5.50 (d, J=1.5 Hz, 1H, 5-H), 5.00 (d, J=1.5 Hz, 1H, 4-H), 4.50-4.48 (m, 1H, 1-H), 4.32 (d, J=7.8 Hz, 1H, 7-Hβ), 3.84 (dd, J=7.0, 5.3 Hz, 1H, 7-Hα), 3.78 (d, J=14.8 Hz, 1H, 13-H), 3.33 (d, J=14.8 Hz, 1H, 13-H), 2.61 (app. s, 2H, 13-H), 2.16 (d, J=15.3 Hz, 1H, 2-H), 1.69 (dd, J=15.3, 4.0 Hz, 1H, 2-H); $^{13}$C NMR (126 MHz, CDCl$_3$): δ 164.7, 136.0 135.6, 133.6, 132.8, 132.5, 132.4, 132.3, 132.0, 131.3, 128.9, 128.5, 126.9, 126.5, 126.2, 99.0, 72.2, 71.8, 66.7, 41.7, 36.4, 34.4, 31.5; FT-IR (neat): 2959, 1732, 1369, 1221, 894, 721 cm$^{-1}$; MS (ESI) m/z: 503.4 [M+H]$^+$, 523.2 [M+Na]$^+$.

(1S,4S,5R)-3,3-Dibenzyl-6,8-dioxabicyclo[3.2.1]octan-4-yl cinnamate (25)

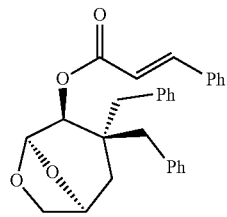

The reaction of 9 (2.0 g, 6.5 mmol) with cinnamoyl chloride (13 mmol) according to the general procedure gave 25 as a colorless solid (1.94 g, 68%). mp 129-131° C.; [α]$_D^{25}$ −164 (c 2.1, CH$_2$Cl$_2$); $^1$H NMR (500 MHz, CDCl$_3$): δ 7.78 (d, J=15.7 Hz, 1H), 7.59-7.56 (m, 1H), 7.44-7.40 (m, 3H), 7.39-7.24 (m, 7H), 7.23-7.18 (m, 2H), 7.07-7.03 (m, 2H), 6.56 (d, J=15.7 Hz, 1H), 5.50 (d, J=1.7 Hz, 1H), 5.09 (d, J=1.7 Hz, 1H), 4.45 (ddd, J=5.2, 4.7, 2.3 Hz, 1H); 4.38 (d, J=7.4 Hz, 1H), 3.84 (dd, J=7.4, 5.2 Hz, 1H); 3.50 (d, J=15.0 Hz, 1H), 3.18 (d, J=15.0 Hz, 1H), 2.74 (d, J=13.5 Hz, 1H), 2.50 (d, J=13.5 Hz, 1H), 1.85-1.81 (m, 2H); $^{13}$C NMR (125 MHz, CDCl$_3$): δ 166.0, 145.8, 138.3, 136.8, 134.4, 132.0 (2C), 131.6 (2C), 130.7, 129.1 (2C), 128.4 (2C), 128.34 (2C), 128.30 (2C), 126.8, 126.6, 117.9, 100.1, 73.5, 68.0, 44.2, 40.6, 40.2, 31.5; FT-IR (neat): ν=2967, 1736, 1369, 1219, 1221 cm⁻¹; MS (ESI) m/z: 441.1 [M+H]⁺, 463.0 [M+Na]⁺; ESI-HRMS Calcd for [M+Na]⁺ C$_{29}$H$_{28}$O$_4$Na: 463.1885; found: 463.1917.

(1S,4S,5R)-3,3-Dibenzyl-6,8-dioxabicyclo[3.2.1]octan-4-yl (E)-but-2-enoate (26)

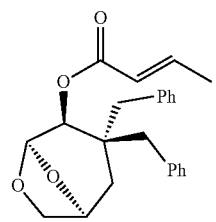

26

The reaction of 9 (100 mg, 0.32 mmol) with crotyl chloride (0.64 mmol) according to the general procedure gave 26 as a colorless wax (82 mg, 67%). [α]$_D^{25}$ −80 (c 1.1, CH$_2$Cl$_2$); ¹H NMR (500 MHz, CDCl$_3$): δ 7.29-7.24 (m, 2H), 7.23-7.10 (m, 6H), 7.00 (dd, J=15.3, 7.2 Hz, 1H), 6.95-6.91 (m, 2H), 5.89 (dd, J=15.3, 2.0 Hz, 1H), 5.36 (d, J=1.9 Hz, 1H), 4.91 (d, J=1.9 Hz, 1H), 4.34 (ddd, J=5.1, 2.3, 2.3 Hz, 1H), 4.27 (d, J=7.5 Hz, 1H) 3.74 (dd, J=7.5, 5.1 Hz, 1H), 3.37 (d, J=14.9 Hz, 1H), 3.02 (d, J=14.9 Hz, 1H), 2.60 (d, J=13.8 Hz, 1H), 2.38 (d, J=13.8 Hz, 1H), 1.86 (dd, J=7.2, 2.0 Hz, 3H), 1.73-1.70 (m, 2H); ¹³C NMR (125 MHz, CDCl$_3$): δ 165.9, 145.9, 138.2, 136.8, 131.9 (2C), 131.6 (2C), 128.28 (2C), 128.25 (2C), 126.7, 126.6, 122.6, 100.1, 73.4, 73.0, 68.0, 44.1, 40.5, 40.1, 31.3, 18.2; FT-IR (neat): ν=2560, 1714, 1654, 1176, 1034, 901 cm⁻¹; MS (ESI) m/z: 401.2 [M+Na]⁺; ESI-HRMS Calcd for [M+Na]⁺ C$_{24}$H$_{26}$O$_4$Na: 401.1729; found: 401.1749.

(1S,4S,5R)-3,3-Dibenzyl-6,8-dioxabicyclo[3.2.1]octan-4-yl methacrylate (27)

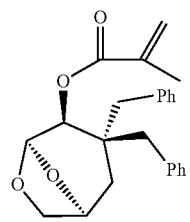

27

The reaction of 9 (100 mg, 1.0 equiv, 0.32 mmol) with methacryl chloride (0.64 mmol) according to the general procedure gave 27 as colorless crystals (102 mg, 85%). mp 120-122; [α]$_D^{25}$ −128 (c 2.0, CH$_2$Cl$_2$); ¹H NMR (500 MHz, CDCl$_3$): δ 7.38-7.33 (m, 2H), 7.32-7.24 (m, 5H), 7.23-7.19 (m, 1H), 7.04-7.00 (m, 2H), 6.21 (dd, J=1.6, 1.6 Hz, 1H), 5.64 (dd, J=1.6, 1.6 Hz, 1H), 5.46 (d, J=1.8 Hz, 1H), 5.00 (d, J=1.8 Hz, 1H), 4.42 (ddd, J=4.9, 3.1, 3.1 Hz, 1H), 4.34 (d, J=7.5 Hz, 1H), 3.82 (dd, J=7.5, 4.9 Hz, 1H), 3.49 (d, J=14.8 Hz, 1H), 3.09 (d, J=14.8 Hz, 1H), 2.72 (d, J=13.6 Hz, 1H), 2.49 (d, J=13.6 Hz, 1H), 2.00 (dd, J=1.6, 1.6 Hz, 3H), 1.81-1.77 (m, 2H); ¹³C NMR (125 MHz, CDCl$_3$): δ 166.8, 138.3, 136.8, 136.3, 131.8 (2C), 131.4 (2C), 128.4 (2C), 128.3 (2C), 126.8, 126.62, 126.55, 99.9, 73.8, 73.4, 68.0, 44.6, 40.7, 39.8, 31.6, 18.5; FT-IR (neat): ν=2960, 1708, 1635, 1164, 1039, 737 cm⁻¹; MS (ESI) m/z: 401.2 [M+Na]⁺; ESI-HRMS Calcd for [M+Na]⁺ C$_{24}$H$_{26}$O$_4$Na: 401.1729; found: 401.1760.

(1S,4S,5R)-1',3'-Dihydro-6,8-dioxaspiro[bicyclo[3.2.1]octane-3,2'-inden]-4-yl acrylate (28)

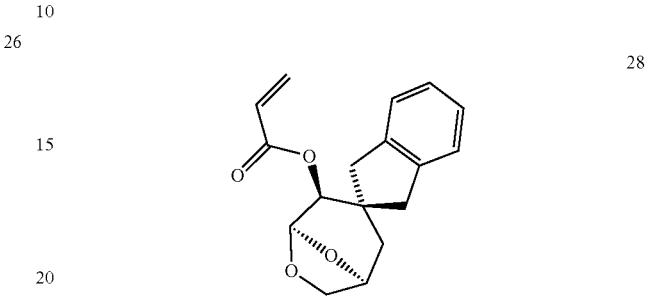

28

The reaction of 17 (100 mg, 1.0 equiv, 0.43 mmol) with acryloyl chloride (0.86 mmol) according to the general procedure followed by recrystallisation in CH$_2$Cl$_2$/hexanes gave 28 as colorless crystals (107 mg, 87%). mp 87-89° C.; [α]$_D^{25}$ −79 ¹H NMR (500 MHz, CDCl$_3$): δ=7.15-7.04 (m, 4H), 6.00 (dd, J=17.4, 1.5 Hz, 1H), 5.75 (dd, J=17.4, 10.4 Hz, 1H), 5.58 (dd, J=10.4, 1.5 Hz, 1H), 5.41 (d, J=1.4 Hz, 1H), 5.00 (d, J=1.4 Hz, 1H), 4.60-4.56 (m, 1H), 4.16 (d, J=7.5 Hz, 1H), 3.87-3.79 (m, 2H), 3.06 (d, J=16.0 Hz, 1H), 2.95 (d, J=16.0 Hz, 1H), 2.85 (d, J=16.1 Hz, 1H), 2.19 (ddd, J=14.6, 4.1, 1.5 Hz, 1H), 1.99 (dd, J=14.6, 1.5 Hz, 1H); ¹³C NMR (125 MHz, CDCl$_3$): δ=165.6, 143.5, 140.5, 131.2, 127.5, 126.4, 126.3, 124.0, 123.8, 100.6, 77.0, 73.9, 67.9, 48.5, 45.9, 41.3, 41.2; FT-IR (neat): ν=2898, 1721, 1404, 1263, 1183, 982, 734 cm⁻¹; MS (ESI) m/z: 309.1 [M+Na]⁺; ESI-HRMS Calcd for [M+Na]⁺ C$_{17}$H$_{18}$O$_4$Na: 309.1103; found: 309.1096.

(1S,4S,5R)-1',3'-Dihydro-6,8-dioxaspiro[bicyclo[3.2.1]octane-3,2'-inden]-4-yl (E)-4,4,4-trifluorobut-2-enoate (29)

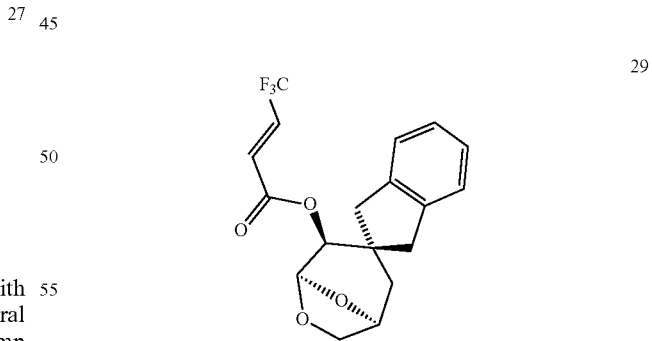

29

The reaction of 17 (100 mg, 1.0 equiv, 0.43 mmol) with 4,4,4-trifluorocrotonic acid (0.43 mmol) according to the general procedure followed by recrystallisation in CH$_2$Cl$_2$/hexanes gave 29 as (139 mg, 91%) as colorless crystals. mp 71-73° C.; [α]$_D^{25}$=−62 ¹H NMR (500 MHz, CDCl$_3$): δ=7.16-7.12 (m, 1H), 7.10-7.02 (m, 3H), 6.09-5.98 (m, 2H), 5.40 (d, J=1.75 Hz, 1H), 5.00 (d, J=1.5 Hz, 1H), 4.63-4.59 (m, 1H), 4.14 (d, J=7.5 Hz, 1H), 3.89 (d, J=15.5 Hz, 1H), 3.87-3.83 (m, 1H), 3.03-2.91 (m, 3H), 2.28 (ddd, J=14.6 Hz, 3.8 Hz, 1.5 Hz, 1H), 2.05 (dd, J=14.5 Hz, 1.5 Hz, 1H). 13C NMR (125 MHz, CDCl$_3$): δ=163.4, 143.7, 140.3, 131.4, 127.4, 126.7, 126.4, 124.0, 123.5, 121.8, 100.4, 78.8, 73.8, 6738, 48.7, 46.1, 41.7, 41.3. FT-IR (neat): ν=3006, 1732, 1308, 1275, 1261, 1136, 750 cm$^{-1}$; MS (ESI) m/z: 378.2 [M+Na]$^+$]$^+$; ESI-HRMS Calcd for [M+Na]$^+$ C$_{18}$H$_{17}$O$_4$F$_3$Na: 377.0977; found: 377.0972.

Example 5—Diels-Alder Reaction of Cyclopentadiene and an Acrylate Ester of a Chiral Auxiliary A chiral auxiliary functionalised with a dienophile may undergo a Diels-Alder reaction with a suitable diene, for example, cyclopentadiene. The Diels-Alder reaction may be catalysed by a Lewis acid. The Diels-Alder reactions of an acrylate ester (i.e. functionalised chiral auxiliary) and cyclopentadiene were performed both with and without Lewis acids according to the following general procedure.

The acrylic ester (1.0 equiv) was dissolved in dry DCM (0.2 M final concentration) under N$_2$ and then cooled to the temperature indicated in Table 1. The Lewis acid was added under N$_2$ and stirred for 20 min at the indicated temperature then freshly distilled cyclopentadiene (5 mmol) was added dropwise and the reaction was left at the temperature indicated in Table 1 for the appropriate time. After 18 h, if the reaction was incomplete a further portion of cyclopentadiene (5 mmol) was added. The reactions without Lewis acid were concentrated after completion. The reactions where Lewis acids were used were quenched by the addition of water and 1 M HCl, then extracted with DCM (×3). The combined organic extracts were dried over MgSO$_4$, filtered and then concentrated under reduced pressure. For all reactions, the residues were absorbed onto a pad of silica (10 g/g ester) and the remaining cyclopentadiene and its corresponding dimer were washed from the silica using hexanes then the product was eluted with EtOAc. The percentage conversion and the diastereomeric ratios were determined by $^1$H NMR spectroscopy, while the endo and exo ratios were determined by $^1$H NMR spectroscopy and GCMS analysis.

TABLE 1

Diels-Alder reactions of acrylate esters with cyclopentadiene.

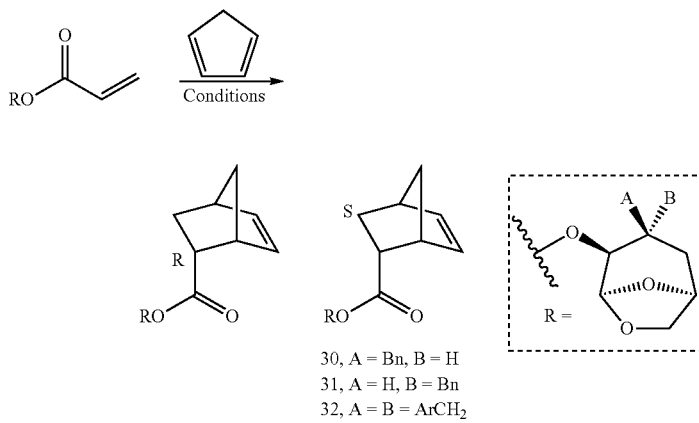

30, A = Bn, B = H
31, A = H, B = Bn
32, A = B = ArCH$_2$

| Entry | Lewis acid (equiv.) | SM | Time [h] | Temp [° C.] | Conc [%] | Product | dr endolexo | dr R/S |
|---|---|---|---|---|---|---|---|---|
| 1 | SnCl$_4$ (1.0) | | 21 | 36 | −13 | >99 | 30 | 93:7 | 82:18 |
| 2 | SnCl$_4$ (1.0) | | 20 | 36 | −13 | >99 | 31 | 93:7 | 54.46 |
| 3 | — | | 22 | 42 | +20 | 92 | 32 | 84:16 | 51:49 |
| 4 | AlCl$_3$ (1.0) | 19a | 18 | −75 | 68 | 32 | 96:4 | 95:5 |
| 5 | AlCl$_3$ (1.0) | 19a | 18 | −13 | 91 | 32 | 88:12 | 94:6 |
| 6 | AlCl$_3$ (1.0) | 19a | 18 | 0 | >99 | 32 | 86:14 | 73:27 |
| 7 | AlCl$_3$ (0.5) | 19a | 18 | −13 | >99 | 32 | 96:4 | 95:5 |
| 8 | AlCl$_3$ (2.0) | 19a | 18 | −13 | 55 | 32 | 93:7 | 75:25 |
| 9 | SnCl$_4$ (1.0) | 19a | 18 | −13 | 97 | 32 | 97:3 | 94:6 |
| 10 | SnCl$_4$ (1.0) | 19a | 18 | −13 | 45 | 32 | 96:4 | 92:8 |
| 11 | SnCl$_4$ (1.0) | 19a | 18 | −13 | 15 | 32 | 94:6 | 68:32 |
| 12 | SnCl$_4$ (0.5) | 19a | 36 | −13 | >99 | 32 | 97:3 | 96:4 |
| 13 | SnCl$_4$ (1.0) | 19a | 36 | −13 | >99 | 32 | 97:3 | 97:3 |
| 14 | BF$_3$ (1.0) | 19a | 24 | −13 | 35 | 32 | 92:8 | 95:5 |
| 15 | EtAlCl$_2$ (1.0) | 19a | 24 | −13 | >99 | 32 | 98:2 | 98:2 |
| 16 | SnCl$_4$ (1.0) | 23 | 36 | −13 | >99 | 33 | 96:4 | 98:2 |
| 17 | SnCl$_4$ (1.0) | 24 | 36 | −13 | >99 | 34 | 95:5 | 84:16 |

(1S,4S,5R)-3,3-Dibenzyl-6,8-dioxabicyclo[3.2.1]octan-4-yl(1R,4R)-bicyclo[2.2.1]hept-5-ene-2-carboxylate (35)

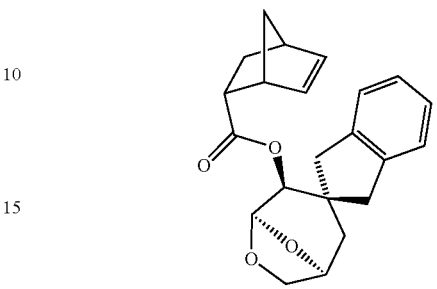

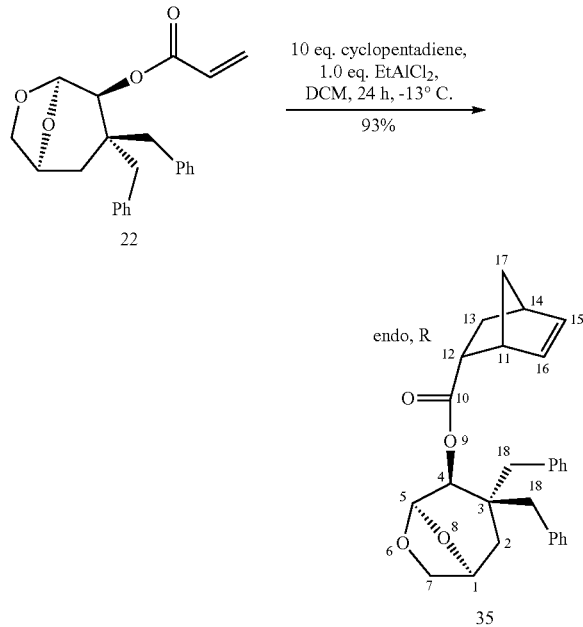

Following the general procedure, acrylate ester 22 (100 mg, 1.0 equiv, 0.28 mmol,) was treated with cyclopentadiene (181 mg, 10 equiv, 2.8 mmol) catalysed by a 1.8 M EtAlCl$_2$ in toluene (150 µL, 1.0 equiv, 0.28 mmol). The product was recrystallised by slow evaporation from dry MeOH to afford 35 as colourless crystals (110 mg, 93%); mp 96-98° C.; $[\alpha]_D^{25}$ −23 (c 1.0, CH$_2$Cl$_2$); 1H NMR (500 MHz, CDCl$_3$): δ 7.37-7.34 (m, 2H, Ar—H), 7.30-7.26 (m, 4H, Ar—H), 7.22-7.20 (m, 2H, Ar—H), 6.97-6.95 (m, 2H, Ar—H), 6.33 (dd, J=5.7, 3.1 Hz, 1H, 15-H), 6.11 (dd, J=5.7, 2.8 Hz, 1H, 16-H), 5.35 (d, J=1.9 Hz, 1H, 5-H), 4.91 (d, J=1.9 Hz, 1H, 4-H), 4.40 (ddd, J=5.5, 5.2, 3.1 Hz, 1H, 1-H), 4.34 (d, J=7.5 Hz, 1H, 7-Hβ), 3.81 (dd, J=7.5, 5.2 Hz, 1H, 7-Hα), 3.46 (d, J=14.5 Hz, 1H, 18-H), 3.37 (br s, 1H, 11-H), 3.15-3.11 (m, 1H, 12-H), 3.12-3.08 (d, J=14.5 Hz, 1H, 18-H), 2.98 (br s, 1H, 14-H), 2.60 (d, J=14.0 Hz, 1H, 18-H), 2.48 (d, J=14.0 Hz, 1H, 18-H), 1.98 (ddd, J=11.8, 9.3, 3.7 Hz, 1H, 13-H), 1.76 (app. d, J=2.9 Hz, 2H, 2-H), 1.57-1.50 (m, 2H, 13-H, 17-H), 1.35 (d, J=8.3 Hz, 1H, 17-H); 13C NMR (126 MHz, CDCl$_3$): δ 174.2, 138.7, 138.2, 136.7, 132.1, 132.0, 131.6, 128.31, 128.29, 126.8, 126.6, 100.1, 73.3, 72.7, 68.0, 50.2, 46.2, 43.8, 42.7, 40.48, 40.45, 30.9, 29.9, 29.2; FT-IR (neat): 2958, 1746, 1356, 1231, 899, 708 cm$^{-1}$; MS (ESI) m/z: 453.1 [M+Na]$^+$.

Example 6—Diels-Alder Reaction of a Tethered Chiral Auxiliary

The Diels-Alder reaction of an acrylate ester bound to a tethered chiral auxiliary was performed with a diene (such as cyclopentadiene, 1,3-cyclohexadiene, butadiene or isoprene) under the same conditions as described in Example 5.

(1S,4S,5R)-1',3'-Dihydro-6,8-dioxaspiro[bicyclo[3.2.1]octane-3,2'-inden]-4-yl (1R,2R,4R)-bicyclo[2.2.1]hept-5-ene-2-carboxylate (36)

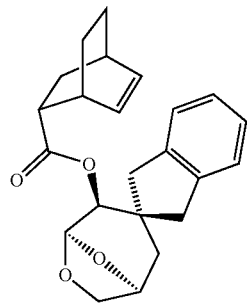

The reaction of 17 (20 mg, 1.0 equiv, 0.07 mmol) with cyclopentadiene and recrystallisation with CH$_2$Cl$_2$:hexanes gave 36 as colorless crystals (20 mg, 82%). mp 95-97° C.; $[\alpha]_D^{25}$ −12 (c 1.0, CH$_2$Cl$_2$); 1H NMR (500 MHz, CDCl$_3$): δ 7.20-7.10 (m, 4H), 6.05 (dd, J=5.7, 3.1 Hz, 1H), 5.34 (dd, J=5.7, 3.1 Hz, 1H), 5.32 (d, J=1.5 Hz, 1H), 4.85 (d, J=1.5 Hz, 1H), 4.56 (ddd, J=4.3, 4.3, 1.7 Hz, 1H), 4.16 (d, J=7.5 Hz, 1H), 3.89 (d, J=15.6 Hz, 1H), 3.80 (ddd, J=6.9, 4.8, 1.3 Hz, 1H), 2.97 (d, J=15.6 Hz, 1H), 2.88 (d, J=15.6 Hz, 1H), 2.78 (brs, 1H), 2.62 (ddd, J=9.1, 3.9, 3.9 Hz, 1H), 2.46 (brs, 1H), 2.18 (ddd, J=14.6, 3.7, 1.2 Hz, 1H), 1.98 (d, J=14.6 Hz, 1H), 1.71 (ddd, J=12.9, 9.2, 3.6 Hz, 1H), 1.27-1.20 (m, 2H), 1.07 (brd, J=8.2 Hz, 1H); 13C NMR (126 MHz, CDCl$_3$): δ 174.4, 143.7, 140.6, 137.7, 132.3, 126.6, 126.4, 124.04, 124.01, 1006, 77.1, 73.9, 67.8, 49.8, 48.8, 45.7, 45.2, 43.1, 42.6, 41.8, 41.4, 29.1; FT-IR (neat): ν=2916, 1720, 1452, 1160, 1130, 902, 701 cm$^{-1}$; MS (ESI) m/z: 375.2 [M+Na]$^+$; ESI-HRMS Calcd for [M+Na]$^+$ C$_{22}$H$_{24}$O$_4$Na: 375.1572; found: 375.1576.

(1S,4S,5R)-1',3'-Dihydro-6,8-dioxaspiro[bicyclo[3.2.1]octane-3,2'-inden]-4-yl (1R,2R,4R)-bicyclo[2.2.2]oct-5-ene-2-carboxylate (37)

The reaction of 17 (20 mg, 1.0 equiv, 0.07 mmol) with 1,3-cyclohexadiene according to the general procedure and recrystallisation with CH$_2$Cl$_2$/hexanes gave 37 as colorless crystals (21 mg, 79%). mp 110-122° C.; $[\alpha]_D^{25}$ −42 (c 1.0, CH$_2$Cl$_2$); 1H NMR (500 MHz, CDCl$_3$): δ 7.19-7.08 (m, 4H), 6.16 (dd, J=7.2, 7.2 Hz, 1H), 5.62 (dd, J=7.2, 7.2 Hz, 1H), 5.31 (d, J=1.5 Hz, 1H), 4.87 (d, J=1.5 Hz, 1H), 4.55 (ddd, J=4.3, 4.3, 1.6 Hz, 1H), 4.15 (d, J=7.5 Hz, 1H), 3.89 (d, J=16.0 Hz, 1H), 3.80 (ddd, J=7.2, 5.3, 1.5 Hz, 1H), 3.03 (d, J=16.1 Hz, 1H), 2.88 (d, J=16.0 Hz, 1H), 2.49-2.44 (m, 1H), 2.23 (dddd, J=12.8, 7.3, 3.0, 2.2 Hz, 1H), 2.19 (ddd, J=14.5, 3.7, 1.4 Hz, 1H), 2.03-2.00 (m, 1H), 1.97 (dd, J=14.5, 1.4 Hz, 1H), 1.57-1.44 (m, 2H), 1.37-1.25 (m, 2H), 1.14-0.98 (m, 2H); $^{13}$C NMR (126 MHz, CDCl$_3$): δ 175.1, 143.8, 140.7, 135.1, 131.3, 126.5, 126.3, 123.94, 123.92, 100.6, 77.2, 73.9, 67.7, 48.7, 45.3, 42.5, 41.7, 41.5, 32.1, 29.5, 29.3, 25.2, 24.3; FT-IR (neat): ν=2926, 1719, 1442, 1125, 910, 710 cm$^{-1}$; MS (ESI) m/z: 389.2 [M+Na]$^+$; ESI-HRMS Calcd for [M+Na]$^+$ C$_{23}$H$_{26}$O$_4$Na: 389.1729; found: 389.1717.

(1S,4S,5R)-1',3'-Dihydro-6,8-dioxaspiro[bicyclo[3.2.1]octane-3,2'-inden]-4-yl (R)-cyclohex-3-ene-1-carboxylate (38)

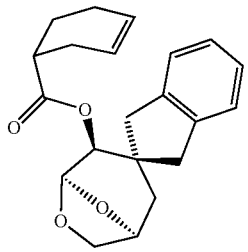

38

The reaction of 17 (20 mg, 1.0 equiv, 0.07 mmol) with butadiene according to the general procedure and recrystallisation from CH$_2$Cl$_2$/hexanes gave 38 as colorless crystals (21 mg, 86%). mp 88-90° C.; [α]$_D^{25}$ −58 (c 1.0, CH$_2$Cl$_2$); $^1$H NMR (500 MHz, CDCl$_3$): δ 7.17-7.05 (m, 4H), 5.58-5.52 (m, 1H), 5.48-5.43 (m, 1H), 5.33 (d, J=1.7 Hz, 1H), 4.94 (d, J=1.7 Hz, 1H), 4.58 (ddd, J=3.9, 3.9, 1.5 Hz, 1H), 4.14 (d, J=8.0 Hz, 1H), 3.87 (d, J=16.4 Hz, 1H), 3.82 (ddd, J=7.7, 4.9, 1.1 Hz, 1H), 3.06 (d, J=16.0 Hz, 1H), 2.94 (d, J=16.0 Hz, 1H), 2.88 (d, J=16.4 Hz, 1H), 2.26-2.19 (m, 1H), 2.12-2.04 (m, 1H), 2.02-1.87 (m, 3H), 1.77-1.60 (m, 3H), 1.43-1.32 (m, 1H); $^{13}$C NMR (126 MHz, CDCl$_3$): δ 175.4, 143.8, 140.7, 126.48, 126.45, 126.3, 125.3, 123.94, 123.85, 100.8, 77.0, 73.9, 67.8, 48.7, 45.7, 41.6, 41.5, 39.0, 26.9, 24.7, 24.4; FT-IR (neat): ν=2920, 1721, 1450, 1150, 1134, 904, 701 cm$^{-1}$; MS (ESI) m/z: 363.2 [M+Na]$^+$; ESI-HRMS Calcd for [M+Na]$^+$ C$_{21}$H$_{24}$O$_4$Na: 363.1572; found: 363.1580.

(1S,4S,5R)-1',3'-Dihydro-6,8-dioxaspiro[bicyclo[3.2.1]octane-3,2'-inden]-4-yl (R)-4-methylcyclohex-3-ene-1-carboxylate (39)

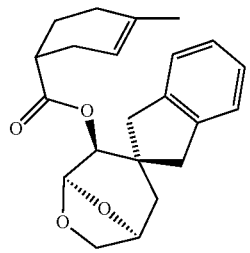

39

The reaction of 17 (20 mg, 1.0 equiv, 0.07 mmol) with isoprene according to the general procedure and recrystallisation from CH$_2$Cl$_2$/hexanes gave 39 as colorless crystals (18 mg, 72%). mp 121-123° C.; [α]$_D^{25}$ −8 (c 1.0, CH$_2$Cl$_2$); $^1$H NMR (500 MHz, CDCl$_3$): δ 7.09-6.98 (m, 4H), 5.26 (brd, J=1.5 Hz, 1H), 5.10-5.06 (m, 1H), 4.87 (brd, J=1.5 Hz, 1H), 4.50 (dd, J=4.2, 4.2 Hz, 1H), 4.07 (d, J=7.4 Hz, 1H), 3.78 (d, J=16.0 Hz, 1H), 3.75 (ddd, J=7.6, 5.5, 1.3 Hz, 1H), 2.98 (d, J=16.4 Hz, 1H), 2.87 (d, J=15.6 Hz, 1H), 2.81 (d, J=16.0 Hz, 1H), 2.17-2.12 (m, 1H), 1.99-1.93 (m, 1H), 1.91 (d, J=15.6 Hz, 1H), 1.81-1.75 (m, 1H), 1.69-1.58 (m, 2H), 1.57-1.50 (m, 2H), 1.49 (s, 3H), 1.38-1.27 (m, 1H); $^{13}$C NMR (126 MHz, CDCl$_3$): δ 174.5, 143.7, 140.6, 133.5, 126.4, 126.2, 123.91, 123.85, 119.3, 100.8, 76.8, 73.9, 67.8, 48.7, 45.6, 41.54, 41.46, 38.9, 29.2, 27.1, 25.1, 23.5; FT-IR (neat): ν=2915, 1734, 1453, 1146, 1140, 914, 705 cm$^{-1}$; MS (ESI) m/z: 377.2 [M+Na]$^+$; ESI-HRMS Calcd for [M+Na]$^+$ C$_{22}$H$_{26}$O$_4$Na: 377.1729; found: 377.1712.

(1S,4S,5R)-1',3'-Dihydro-6,8-dioxaspiro[bicyclo[3.2.1]octane-3,2'-inden]-4-yl (1R,2S,3S,4S)-3-(trifluoromethyl)bicyclo[2.2.1]hept-5-ene-2-carboxylate (40)

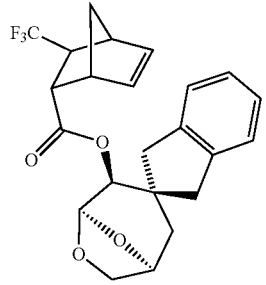

40

The reaction of 17 (25 mg, 1.0 equiv, 0.07 mmol) with cyclopentadiene according to the general procedure and recrystallisation from CH$_2$Cl$_2$/hexanes gave 40 as a colorless wax (20 mg, 67%). [α]$_D^{25}$ −29 (c 1.0, CH$_2$Cl$_2$); $^1$H NMR (500 MHz, CDCl$_3$): δ 7.14-7.02 (m, 4H), 6.09 (dd, J=5.8, 3.2 Hz, 1H), 5.34 (dd, J=5.8, 3.2 Hz, 1H), 5.27 (d, J=1.4 Hz, 1H), 4.80 (d, J=1.4 Hz, 1H), 4.51 (ddd, J=5.5, 4.2, 1.8 Hz, 1H), 4.09 (d, J=7.7 Hz, 1H), 3.87 (d, J=15.5 Hz, 1H), 3.75 (ddd, J=7.5, 5.0, 1.5 Hz, 1H), 2.95 (d, J=15.7 Hz, 1H), 2.94 (brs, 1H), 2.88 (d, J=16.8 Hz, 1H), 2.87 (d, J=15.7 Hz, 1h), 2.86 (brs, 1H), 2.68 (dd, J=5.2, 3.6 Hz, 1H), 2.27 (brs, 1h), 2.17-2.13 (m, 2H), 1.96-1.91 (m, 1H), 1.42 (d, J=8.3 Hz, 1H); $^{13}$C NMR (126 MHz, CDCl$_3$): δ 172.0, 143.7, 140.5, 137.7, 135.2, 126.7, 126.5, 124.0, 123.9, 100.4, 78.4, 73.9, 67.7, 49.0, 47.5, 46.4, 46.2, 45.6, 45.3, 44.9, 42.1, 41.7, 29.9; FT-IR (neat): ν=2915, 1734, 1453, 1146, 1140, 914, 705 cm$^{-1}$; MS (ESI) m/z: 443.1 [M+Na]$^+$; ESI-HRMS Calcd for [M+Na]$^+$ C$_{21}$H$_{24}$F$_3$O$_4$Na: 443.1446; found: 443.1443.

Example 7—Cycloaddition Chemistry Using a Chiral Auxiliary

A chiral auxiliary of the present invention may be bound to an acrylate ester and the resulting chiral ester used in conjugate addition reaction. The conjugate addition product may be cleaved from the chiral auxiliary and used in subsequent synthetic steps. For example, a suitable substrate functionalized with a chiral auxiliary according to the present invention and further reacted as part of a route to more complex compounds. Examples of such compounds may include ticagrelor (a platelet aggregation inhibitor) and SC-52491 (a serotonergic adamantine), based on the schemes below.

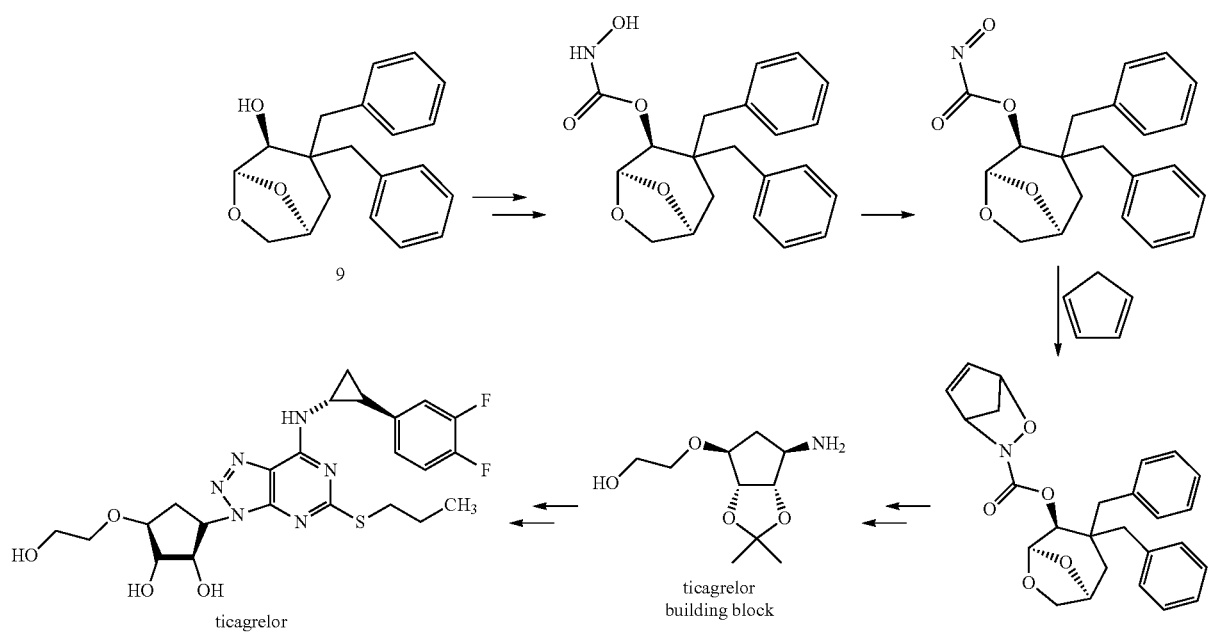

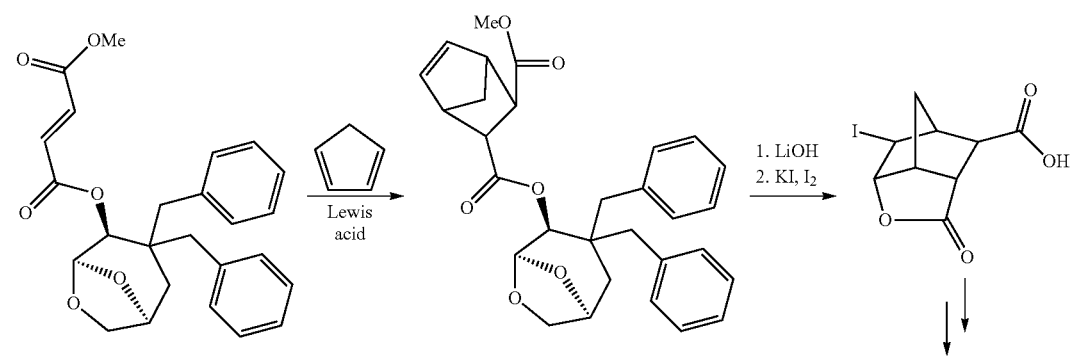

Example 8—Michael Reaction of a Dienophile-Chiral Auxiliary and a Thiol

A chiral auxiliary with an appropriate functional group may be substrates in other reactions, such as Michael reactions.

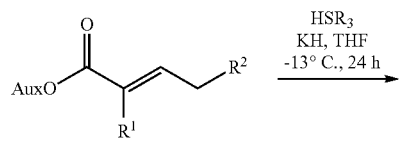

-continued

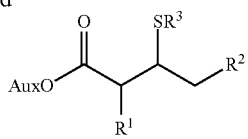

In a dry Schlenk tube under $N_2$ atmosphere was added KH (1.0 equiv, 35% w/w in paraffin) and the suspension washed two times with hexanes (1 mL/100 mg KH) and dried in vacuo. The solid hydride was dissolved in THF (5 mL/mmol ester) and the auxiliary ester (1.0 equiv) was then added. The solution was cooled down to −20° C. and the thiol (10 equiv) was added dropwise (solid thiols where dissolved in THF (1 mL/100 mg thiol)). The reaction mixture was then stirred at −13° C. for 24 h, quenched with 5% w/w NaOH solution and extracted with CH$_2$C$_2$ (3×15 mL/mmol ester). The organic layers were combined, dried with Na$_2$SO$_4$ and concentrated. The residue was purified by column chromatography on silica (EtOAc:hexanes 1:4) and then further purified as specified.

(1S,4S,5R)-3,3-Dibenzyl-6,8-dioxabicyclo[3.2.1] octan-4-yl (S)-3-phenyl-3-(phenylthio)propanoate (41)

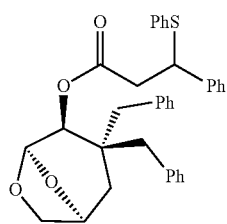

The reaction of 25 (1.0 g, 1.0 equiv, 2.27 mmol) and HSPh (0.97 mL, 2.5 equiv, 5.67 mmol) according to the general procedure gave 41 as a colorless wax (1.15 g, 92%, ratio isomers 89:11). $^1$H NMR (500 MHz, CDCl$_3$): δ 7.33-7.14 (m, 14H), 7.10-7.05 (m, 4H), 6.66-6.60 (m, 2H), 5.20 (d, J=1.8 Hz, 1H), 4.71 (d, J=1.8 Hz, 1H), 4.68 (dd, J=9.0, 7.1 Hz, 1H), 4.29 (ddd, J=5.1, 4.4, 1.0 Hz, 1H), 4.23 (d, J=7.6 Hz, 1H), 3.70 (dd, J=7.1, 5.1 Hz, 1H), 3.25 (d, J=14.6 Hz, 1H), 3.02-2.98 (m, 2H), 2.80 (d, J=14.6 Hz, 1H), 2.15 (dd, J=13.1, 13.1 Hz, 2H), 1.67-1.58 (m, 2H); $^{13}$C NMR (125 MHz, CDCl$_3$): δ 170.3, 140.2, 138.0, 136.5, 133.7, 133.2 (2C), 132.0 (2C), 131.6, 129.1 (2C), 128.8 (2C), 128.2 (2C), 128.11 (2C), 128.06 (2C), 128.01 (2C), 127.96, 126.63, 126.58, 99.8, 73.3, 67.9, 49.5, 43.4, 41.6, 40.31, 40.26, 31.0, 29.8; FT-IR (neat): ν=2920, 1732, 1264, 1134, 903, 734, 700 cm$^{-1}$; MS (ESI) m/z: 573.3 [M+Na]$^+$; ESI-HRMS Calcd for [M+Na]$^+$ C$_{35}$H$_{34}$O$_4$SNa: 573.2075; found: 573.2051.

Minor Isomer: $^1$H NMR (500 MHz, CDCl$_3$, partial): δ 6.76-6.73 (m, 2H), 5.16 (d, J=2.0 Hz, 1H), 4.78 (d, J=2.0 Hz, 1H), 2.27 (d, J=13.4 Hz, 1H), 2.22 (d, J=13.4 Hz, 1H).

(1S,4S,5R)-3,3-Dibenzyl-6,8-dioxabicyclo[3.2.1] octan-4-yl (R)-3-(phenylthio)butanoate (42)

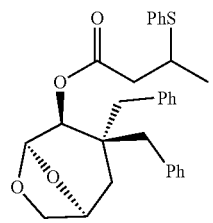

The reaction of 26 (100 mg, 1.0 equiv, 0.26 mmol) and HSPh (260 μL, 10.0 equiv, 2.6 mmol) according to the general procedure gave 42 as a colorless wax (118 mg, 93%, ratio isomers 81:19). $^1$H NMR (500 MHz, CDCl$_3$): δ 7.50-7.45 (m, 2H), 7.36-7.19 (m, 11H), 7.05-7.02 (m, 2H), 5.40 (d, J=1.7 Hz, 1H), 4.98 (d, J=1.7 Hz, 1H), 4.42 (ddd, J=4.9, 2.3, 2.3 Hz, 1H), 4.34 (d, J=7.7 Hz, 1H), 3.81 (dd, J=7.7, 4.9 Hz, 1H), 3.74-3.70 (m, 1H), 3.40 (d, J=15.1 Hz, 1H), 3.06 (d, J=15.1 Hz, 1H), 2.72 (d, J=13.7 Hz, 1H), 2.70 (dd, J=15.4, 7.2 Hz, 1H), 2.61 (dd, J=15.4, 7.2 Hz, 1H), 2.41 (d, J=13.7 Hz, 1H), 1.81-1.77 (m, 2H), 1.41 (d, J=7.2 Hz, 3H); $^{13}$C NMR (125 MHz, CDCl$_3$): δ 170.7, 138.1, 136.8, 132.0 (2C), 131.9 (2C), 131.6 (2C), 129.2 (2C), 128.3 (2C), 128.2 (2C), 127.6, 126.8, 126.7, 99.9, 73.6, 73.4, 68.0, 44.0, 42.1, 40.4, 40.1, 39.4, 31.5, 29.8, 21.3; FT-IR (CH$_2$Cl$_2$): ν=2923, 1453, 1137, 1026, 749, 704 cm$^{-1}$; MS (ESI) m/z: 511.2 [M+Na]$^+$; ESI-HRMS Calcd for [M+Na]$^+$ C$_{30}$H$_{32}$O$_4$SNa: 511.1919; found: 511.1918.

Minor Isomer: $^1$H NMR (500 MHz, CDCl$_3$, partial): δ 5.36 (d, J=1.2 Hz, 1H), 3.21 (dd, J=12.8 Hz, 1H), 1.33 (d, J=7.1 Hz, 3H).

(1S,4S,5R)-3,3-Dibenzyl-6,8-dioxabicyclo[3.2.1] octan-4-yl 2-methyl-3-(phenylthio)propanoate (43)

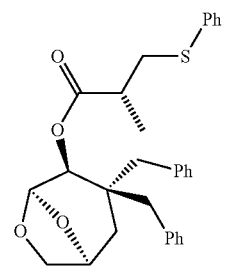

The reaction of 27 (100 mg, 1.0 equiv, 0.26 mmol) and HSPh (260 μL, 10.0 equiv, 2.6 mmol) according to the general procedure gave 43 as a colorless wax (120 mg, 94%, ratio isomers 71:29). $^1$H NMR (500 MHz, CDCl$_3$): δ 7.42-7.38 (m, 2H), 7.34-7.27 (m, 7H), 7.23-7.18 (m, 4H), 7.08-7.04 (m, 2H), 5.39 (d, J=2.1 Hz, 1H), 4.99 (d, J=2.1 Hz, 1H), 4.42 (dd, J=4.7, 2.9, 2.9 Hz, 1H), 4.33 (d, J=7.4 Hz, 1H), 3.81 (dd, J=7.5, 4.8 Hz, 1H), 3.38 (d, J=14.8 Hz, 1H), 3.30 (dd, J=13.2, 8.2 Hz, 1H), 3.10 (dd, J=13.2, 8.2 Hz, 1H), 3.02 (d, J=14.8 Hz, 1H), 2.90 (ddddd, J=8.2, 8.2, 7.1, 7.1, 7.1 Hz, 1H), 2.73 (d, J=14.8 Hz, 1H), 2.43 (d, J=14.8 Hz, 1H), 1.81-1.78 (m, 2H), 1.35 (d, J=7.1 Hz, 3H); $^{13}$C NMR (125 MHz, CDCl$_3$): δ 174.4, 138.1, 131.9, 131.7, 131.6, 130.4, 129.8 (2C), 129.20 (2C), 129.18, 128.3 (2C), 128.2 (2C), 126.7 (2C), 126.6 (2C), 98.8, 73.4, 73.3, 67.9, 43.9, 40.4, 40.1, 40.0, 37.6, 31.1, 17.0; FT-IR (CH$_2$Cl$_2$): ν=2920, 1731, 1453, 1135, 905, 739, 702 cm$^{-1}$; MS (ESI) m/z: 511.3 [M+Na]$^+$; ESI-HRMS Calcd for [M+Na]$^+$ C$_{30}$H$_{32}$O$_4$SNa: 511.1919; found: 511.1925.

Minor Isomer: $^1$H NMR (500 MHz, CDCl$_3$, partial): δ 5.33 (d, J=1.4 Hz, 1H), 4.90 (d, J=1.4 Hz, 1H), 2.74 (dddd, J=8.2, 8.2, 7.1, 7.1, 7.1 Hz, 1H), 1.31 (d, J=7.1 Hz, 3H).

(1S,4S,5R)-3,3-Dibenzyl-6,8-dioxabicyclo[3.2.1] octan-4-yl (S)-3-((2-aminophenyl)thio)-3-phenylpropanoate (44)

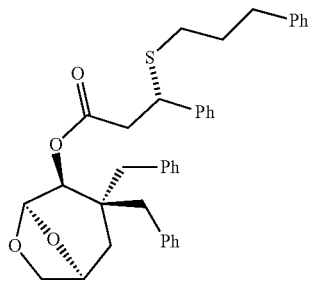

The reaction of 25 (100 mg, 1.0 equiv, 0.23 mmol) and 3-phenylpropane-1-thiol (350 mg, 10.0 equiv, 2.3 mmol) according to the general procedure gave 44 as colorless wax (124 mg, 91%, ratio isomers 71:29). 1H NMR (500 MHz, CDCl$_3$): δ 7.42-7.27 (m, 8H), 7.26-7.14 (m, 8H), 7.10-7.07 (m, 2H), 6.76-6.71 (m, 2H), 5.30 (d, J=1.7 Hz, 1H), 4.80 (d, J=1.7 Hz, 1H), 4.40-4.30 (m, 3H), 3.79 (dd, J=8.2, 4.6 Hz, 1H), 3.33 (d, J=13.8 Hz, 1H), 3.06-3.00 (m, 2H), 2.90 (d, J=13.8 Hz, 1H), 2.68-2.56 (m, 2H), 2.44-2.33 (m, 2H), 2.28 (d, J=13.8 Hz, 1H), 2.21 (d, J=13.8 Hz, 1H), 1.87-1.80 (m, 2H), 1.76-16.5 (m, 2H); $^{13}$C NMR (125 MHz, CDCl$_3$): δ 170.3, 141.5, 141.2, 138.0, 136.5, 132.0 (2C), 131.6 (2C), 128.9 (2C), 128.6 (2C), 128.5 (2C), 128.2 (2C), 128.1 (2C), 128.0 (2C), 127.8, 127.7, 126.62, 126.56, 126.0, 99.8, 73.3, 67.9, 45.8, 43.4, 41.9, 40.3, 40.2, 34.9, 31.0, 30.9, 30.8; FT-IR: ν=2987, 1731, 1504, 1132, 902 748 cm$^{-1}$; MS (ESI) m/z: 615.3 [M+Na]$^+$]$^+$ESI-HRMS Calcd for [M+Na]$^+$ C$_{38}$H$_{40}$O$_4$NSNa: 615.2545; found: 615.2571.

Minor Isomer: $^1$H NMR (500 MHz, CDCl$_3$, partial): δ 6.90-6.87 (m, 2H), 5.26 (d, J=1.7 Hz, 1H), 4.89 (d, J=1.7 Hz, 1H).

Example 9—Oxidation of a Michael Reaction Product

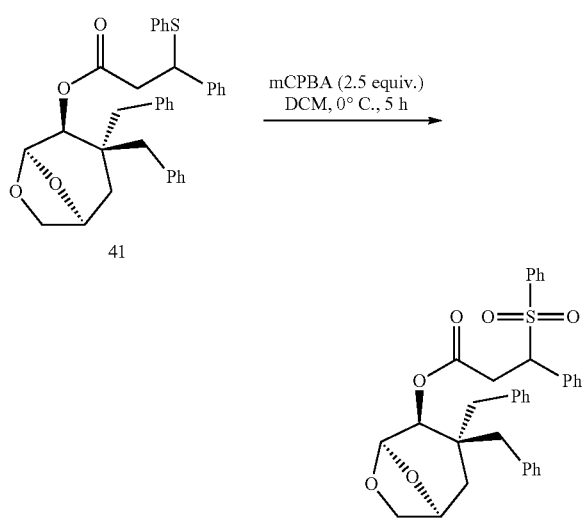

A product obtained from the Michael reaction between a dienophile-chiral auxiliary and a thiol contains a thio functionality that can be oxidised to the corresponding sulfoxide in the presence of m-CPBA. The sulphide (1.0 equiv.) was dissolved in CH$_2$Cl$_2$ and the solution was cooled to 0° C. Then m-CPBA (2.5 equiv.) dissolved in CH$_2$Cl$_2$ was added dropwise. The reaction mixture was stirred for 5 h at 0° C. and then 10% Na$_2$S$_2$O$_3$ was added followed by sat. NaHCO$_3$. The organic layer was dried with MgSO$_4$ and then concentrated. The resulting residue was further purified by column chromatography on silica. The chiral auxiliary tolerates the oxidation process.

(1S,4S,5R)-3,3-Dibenzyl-6,8-dioxabicyclo[3.2.1] octan-4-yl (S)-3-phenyl-3-(phenylsulfonyl) propanoate

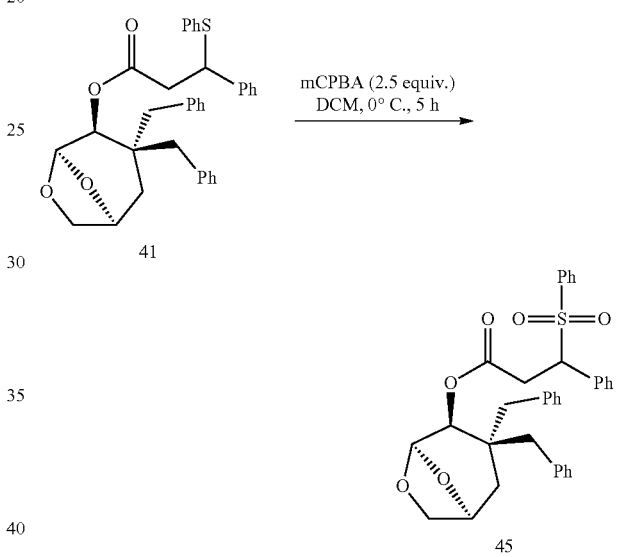

The sulphide 41 (100 mg, 1.0 equiv, 0.18 mmol, ratio of diastereomers 89:11) was dissolved in CH$_2$Cl$_2$ (5 mL) and the solution was cooled down to 0° C. Then m-CPBA (120 mg, 2.5 equiv, 0.40 mmol) dissolved in CH$_2$Cl$_2$ (3 mL) was added dropwise. The reaction mixture was stirred for 5 h at 0° C. and then 10% Na$_2$S$_2$O$_3$ (5 mL) was added followed by sat. NaHCO$_3$ (5 mL). The organic layer was dried with MgSO$_4$ and then concentrated. The resulting residue was further purified by column chromatography on silica (EtOAc:hexanes 1:2) yielding 45 (70 mg, 67%, d.r >98:2) as a colorless solid. mp 118-120° C.; [α]$_D^{25}$ −18 (c 1.0, CH$_2$Cl$_2$); $^1$H NMR (500 MHz, CDCl$_3$): δ 7.63-7.57 (m, 3H), 7.46-7.19 (m, 12H), 7.11-7.02 (m, 3H), 6.56-6.50 (m, 2H), 5.21 (d, J=1.8 Hz, 1H), 4.69 (dd, J=11.0, 5.0 Hz, 1H), 4.68 (d, J=1.8 Hz, 1H), 4.36 (ddd, J=4.7, 4.7, 1.8 Hz, 1H), 4.29 (d, J=7.6 Hz, 1H), 3.77 (dd, J=7.6, 4.7 Hz, 1H), 3.49 (dd, J=15.6, 5.0 Hz, 1H), 3.30 (d, J=14.4 Hz, 1H), 3.28 (dd, J=15.6, 11.0 Hz, 1H), 2.95 (d, J=14.4 Hz, 1H), 2.25 (d, J=13.5 Hz, 1H), 2.18 (d, J=13.5 Hz, 1H), 1.72-1.65 (m, 2H); $^{13}$C NMR (125 MHz, CDCl$_3$): δ 169.3, 137.8, 136.2, 134.0, 131.8 (2C), 131.4, 131.3 (2C), 129.9 (2C), 129.5, 129.2 (2C), 128.9 (2C), 128.7 (2C), 128.1 (2C), 128.0 (2C), 126.53, 126.51, 99.5, 74.0, 73.2, 67.8, 67.4, 43.6, 40.23, 40.16, 33.9, 31.3, 29.7; FT-IR (neat): ν=2988, 1724, 1606, 1450, 1262, 1202, 1139, 980, 733, 703 cm$^{-1}$; MS (ESI) m/z: 605.1 [M+Na]$^+$; ESI-HRMS Calcd for [M+Na]$^+$ C$_{35}$H$_{34}$O$_6$SNa: 605.1974; found: 605.1984.

Example 10—Hydrolysis of a Diels-Alder Cycloadduct to Remove Chiral Auxiliary

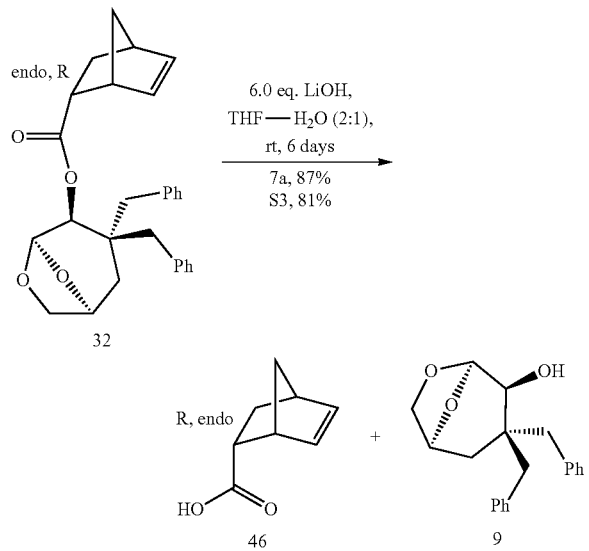

The chiral auxiliary can be removed once the desired stereochemistry has been obtained. This can be achieved by treatment of the substrate with LiOH in a mixture of THF/water. The chiral auxiliary can subsequently be reisolated and reused.

Hydrolysis of Cycloadduct 32

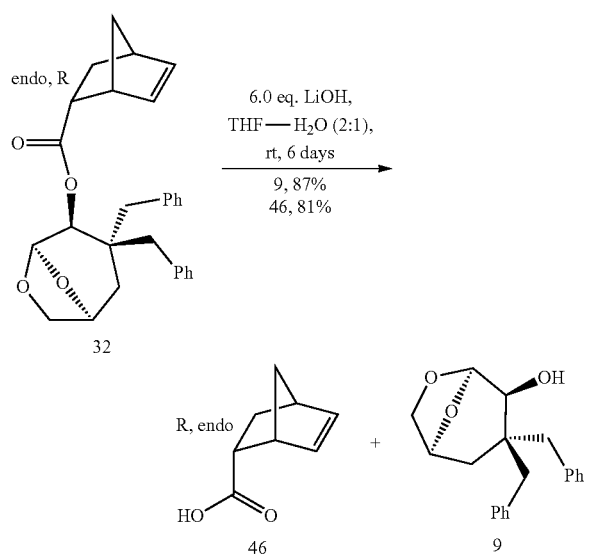

Diels-Alder adduct 32 (50 mg, 1.0 equiv, 0.12 mmol) was dissolved in THF-H$_2$O (2:1, 1.5 mL) and LiOH (20 mg, 6.0 equiv, 0.70 mmol) was added. The reaction mixture was stirred at ambient temperature for 6 days then EtOAc (10 mL) and water (10 mL) were added and the layers separated. The organic layer was dried with MgSO$_4$, filtered then concentrated under reduced pressure and 9 recrystallised from EtOAc/hexanes (1:4) to give colourless crystals (37 mg, 87% recovery). The aqueous layer from the extraction was acidified to pH 2 and extracted with EtOAc (3×10 mL). The organic phase was dried over MgSO$_4$ and concentrated and the residue purified by flash chromatography (EtOAc/hexanes 4:6) to give 46 (13 mg, 81%); [α]$_D^{25}$+134 (c 1.3, CHCl$_3$) (lit. +149.9 (c 2.0, CHCl$_3$); $^1$H NMR (500 MHz, CDCl$_3$): δ 11.75 (br, 1H), 6.21 (dd, J=5.0, 3.0 Hz, 1H), 6.02 (dd, J=5.0, 3.0 Hz, 1H), 3.24 (s, 1H), 2.98 (dt, J=9.5, 4.0 Hz, 1H), 2.92 (s, 1H), 1.19-1.95 (m, 1H), 1.44-1.47 (m, 1H), 1.39-1.43 (m, 1H), 1.29 (d, J=8.0 Hz, 1H).

Example 11—Synthesis of a Chiral Resolving Agent

The compounds depicted below may be used to determine the enantiomeric excess of a mixture of enantiomers. For example, the carboxylic acid functionality may react accordingly with a chiral alcohol where a mixture of enantiomers is present. The diastereomeric esters formed from the reaction may be quantified in order to determine the enantiomeric excess of the mixture of alcohols. Other mixtures of chiral compounds may be analysed accordingly.

2-({[(1S,4S,5R)-3,3-Dibenzyl-6,8-dioxabicyclo[3.2.] octan-4-yl]oxy}carbonyl)benzoic acid (47)

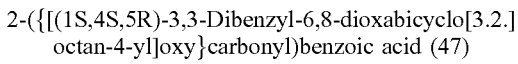

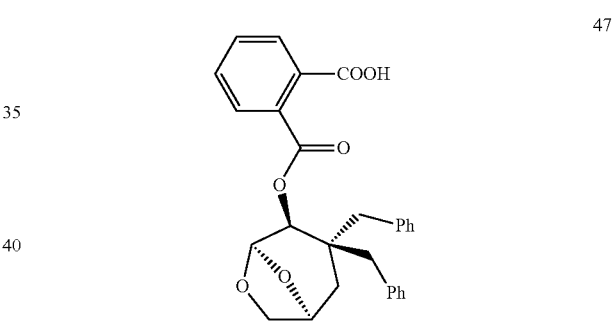

A stirred solution of 9 (100 mg, 0.32 mmol, 1.0 eq), DMAP (4 mg, 0.03 mmol, 0.1 eq), phthalic anhydride (119 mg, 0.80 mmol, 2.5 eq) and pyridine (1.0 mL, 1.24 mmol, 3.9 eq) was heated at 190° C. for 1 h under microwave condition in a sealed vial. The mixture was allowed to cool to room temperature and was then dissolved in CH$_2$Cl$_2$ (15 mL) and washed with HCl (1 M, 15 mL) then brine (15 mL). The product was dried over MgSO$_4$, filtered and concentrated under vacuum. Flash column chromatography (50:1:1 CH$_2$Cl$_2$/MeOH/AcOH) afforded 47 as a white solid (86 mg, 59% yield, 90% conversion); mp 180-182° C.; [α$_D$]$^{29}$=−141 (1.0, CH$_2$Cl$_2$); $^1$H NMR (500 MHz, CDCl$_3$) δ 7.88 (dd, J=7.3, 1.2 Hz, 1H), 7.72 (dd, J=7.3, 1.6 Hz, 1H), 7.64-7.58 (m, 2H), 7.30-7.19 (m, 8H), 7.09-7.08 (m, 2H), 5.61 (d, J=1.7 Hz, 1H), 5.21 (d, J=1.7 Hz, 1H), 4.44 (dddd, J=4.6, 3.0, 1.7, 1.7 Hz, 1H), 4.36 (d, J=7.3 Hz, 1H), 3.82 (dd, J=7.3, 4.6 Hz, 2H), 3.43 (d, J=14.5 Hz, 1H), 3.06 (d, J=14.5 Hz, 1H), 2.76 (d, J=13.6 Hz, 1H), 2.47 (d, J=13.6 Hz, 1H), 1.85 (dd, J=15.1, 3.0 Hz, 1H), 1.81 (dd, J=15.1, 1.7 Hz, 1H); $^{13}$C NMR (125 MHz, CDCl$_3$) δ 170.6, 167.5, 138.1, 136.8, 133.0, 132.1, 131.9, 131.6, 131.3, 130.7, 130.0, 129.2, 128.4, 128.2, 126.8, 126.5, 99.6, 74.7, 73.5, 68.0, 44.2, 40.5, 40.0, 31.6; FT-IR (in CH$_2$Cl$_2$) ν=2949, 1728, 1603, 1584, 1492, 1458, 1285, 1266, 1127, 1079, 1040, 982, 905, 872, 766, 751, 703 cm$^{-1}$; ESIMS m/z 481.2 [M+Na]$^+$; HRMS (ESI) calcd for $C_{28}H_{26}O_6Na^+$[M+Na]$^+$481.1627, found 481.1633.

tert-Butyl {[(1S,4S,5R)-3,3-dibenzyl-6,8-dioxabicyclo[3.2.1]octan-4-yl]oxy}acetate (48)

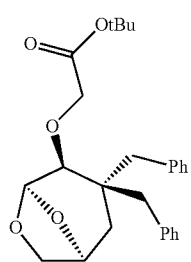

To a stirred solution of 9 (1.08 g, 3.48 mmol, 1.0 eq) in dry THF (10 mL) was added sodium hydride (264 mg, 6.61 mmol, 1.9 eq) and then tert-butyl bromoacetate (1.0 mL, 6.79 mmol, 2.0 eq). The mixture was stirred at 20° C. for 24 h and then the reaction mixture was washed with water (50 mL), extracted with CH$_2$Cl$_2$ (3×20 mL), dried over MgSO$_4$, filtered and concentrated under vacuum. Flash column chromatography (1:4 EtOAc/petroleum ether) afforded 48 as a colourless oil (450 mg, 30% yield); $[C_D]^{21.5}$=−127 (1.0, CH$_2$Cl$_2$); $^1$H NMR (500 MHz, CDCl$_3$) δ 7.34-7.31 (m, 2H), 7.29-7.24 (m, 5H), 7.22-7.19 (m, 1H), 7.02-7.01 (m, 2H), 5.51 (d, J=1.6 Hz, 1H), 4.39 (ddd, J=4.8, 2.9, 2.9 Hz, 1H), 4.34 (d, J=7.5 Hz, 1H), 4.22 (d, J=16.1 Hz, 1H), 4.17 (d, J=16.1 Hz, 1H), 3.82 (dd, J=7.5, 4.8 Hz, 1H), 3.35 (d, J=14.5 Hz, 1H), 3.32 (d, J=1.6 Hz, 1H), 3.23 (d, J=14.5 Hz, 1H), 2.96 (d, J=13.5 Hz, 1H), 2.37 (d, J=13.5 Hz, 1H), 1.79-1.72 (m, 2H), 1.54 (s, 9H); $^{13}$C NMR (125 MHz, CDCl$_3$) δ 169.7, 138.7, 137.9, 132.1, 131.5, 128.2, 128.0, 126.5, 126.2, 99.8, 81.9, 80.8, 73.5, 68.6, 68.0, 44.0, 41.6, 39.8, 30.8, 28.3; FT-IR (in CH$_2$Cl$_2$) ν=3026, 2975, 1747, 1723, 1602, 1495, 1452, 1393, 1368, 1306, 1259, 1226, 1161, 1116, 1049, 1033, 1004, 979, 905, 847, 823, 766, 749, 703, 667 cm$^{-1}$; ESIMS m/z 447.2 [M+Na]$^+$; HRMS (ESI) calcd for $C_{26}H_{32}O_5Na^+$ [M+Na]$^+$447.2147, found 447.2142.

{[(1S,4S,5R)-3,3-Dibenzyl-6,8-dioxabicyclo[3.2.1]octan-4-yl]oxy}acetic acid (49)

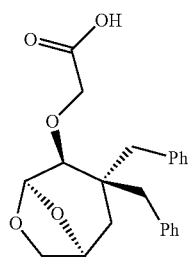

To a well-stirred solution of NaOH in water (4 M, 20 mL) was added dropwise to 9 (0.45 g, 0.98 mmol, 1.0 eq, in 4 mL of EtOH). The mixture was heated at 80° C. for 24 h. The aqueous layer was washed with CH$_2$Cl$_2$ (1×15 mL), then acidified to pH=4.00 with HCl (8 M). The product was extracted with CH$_2$Cl$_2$ (3×15 mL), dried over MgSO$_4$, filtered and concentrated under vacuum. Flash column chromatography (50:1:1 CH$_2$Cl$_2$/MeOH/AcOH) afforded 49 as a white solid (120 mg, 33% yield); mp 71-73° C.; $[\alpha_D]^{20.5}$=−76 (1.0, CH$_2$Cl$_2$); $^1$H NMR (500 MHz, CDCl$_3$) δ 8.57 (br s, 1H), 7.35-7.32 (m, 2H), 7.30-7.27 (m, 5H), 7.24-7.21 (m, 1H), 7.03-7.01 (m, 2H), 5.52 (br s, 1H), 4.43 (ddd, J=4.6, 2.9, 2.9 Hz, 1H), 4.35 (d, J=7.5 Hz, 1H), 4.33-4.31 (m, 2H), 3.84 (dd, J=7.5, 4.6 Hz, 1H), 3.40 (d, J=1.5 Hz, 1H), 3.33 (d, J=14.5 Hz, 1H), 3.21 (d, J=14.5 Hz, 1H), 2.92 (d, J=13.6 Hz, 1H), 2.40 (d, J=13.6 Hz, 1H), 1.83-1.77 (m, 2H); $^{13}$C NMR (125 MHz, CDCl$_3$) 174.0, 138.3, 137.6, 132.0, 131.3, 128.4, 128.1, 126.7, 126.4, 99.1, 80.9, 73.5, 68.0, 67.5, 44.3, 41.6, 39.7, 31.3; FT-IR (in CH$_2$Cl$_2$) ν=3036, 2935, 1733, 1492, 1454, 1353, 1223, 1117, 1035, 978, 958, 905, 824, 771, 751, 708, 665 cm$^{-1}$; ESIMS m/z 391.1 [M+Na]$^+$; HRMS (ESI) calcd for $C_{22}H_{24}O_5Na^+$[M+Na]$^+$391.1521, found 391.1497.

Example 12—Resolution of Enantiomers Using a Chiral Resolving Agent

A compound according to the present invention may be used as a resolving agent to produce diastereomers that may be separable by techniques such as crystallisation or chromatography.

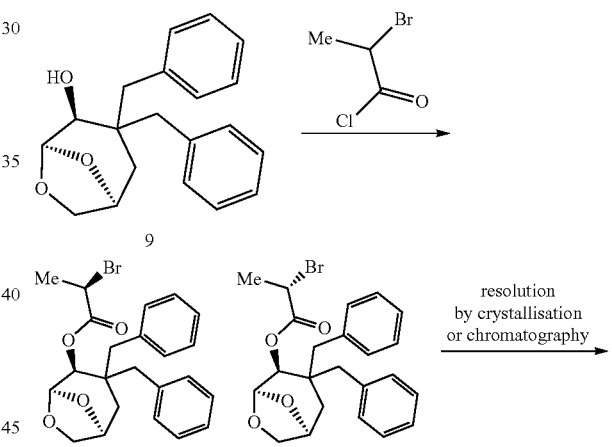

The claims defining the invention are as follows:

1. An enantiomerically enriched compound of the general formula (I):

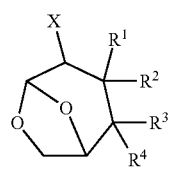

or a salt thereof, wherein:
R$^1$ and R$^2$ are independently selected from the group consisting of H, optionally-substituted alkyl, optionally-substituted aryl, optionally-substituted heteroaryl, optionally-substituted heterocyclyl, optionally-substituted arylalkyl, optionally-substituted heterocyclylalkyl, optionally-substituted heteroarylalkyl, optionally-substituted alkenyl, and optionally-substituted alkynyl;

wherein one of $R^1$ and $R^2$ is optionally-substituted aryl or optionally-substituted arylalkyl or $R^1$ and $R^2$ taken together form a spirocyclic group;

$R^3$ and $R^4$, where present, may be the same or different and are selected from the group consisting of H, optionally-substituted alkyl, optionally-substituted alkenyl, optionally-substituted alkynyl, optionally-substituted aryl, optionally-substituted heteroaryl, optionally-substituted heterocyclyl, optionally-substituted heteroarylalkyl, optionally-substituted benzyl, optionally-substituted silyl, optionally-substituted acyl, optionally-substituted alkoxy and $NR^5R^6$;

wherein at least one of $R^1$, $R^2$, $R^3$ and $R^4$ is not H;

$R^5$ and $R^6$ may be the same or different and are selected from the group consisting of H, optionally-substituted aryl, optionally-substituted alkyl and $SO_2R^7$;

$R^7$ is H, alkyl or aryl;

X is $NHR^8$, $OR^8$ or $SR^8$; and $R^8$ is H or comprises a prochiral reactive group.

2. An enantiomerically enriched compound according to claim 1, wherein one of $R^1$ and $R^2$ is optionally-substituted benzyl.

3. An enantiomerically enriched compound of claim 2, wherein one of $R^1$ and $R^2$ is optionally-substituted benzyl and is in a syn-relationship with respect to X.

4. An enantiomerically enriched compound according to claim 1, wherein $R^1$ and $R^2$ are each independently substituted with one or more halogen groups.

5. An enantiomerically enriched compound according to claim 1, wherein $R^1$ and $R^2$ taken together form a spirocyclic compound.

6. An enantiomerically enriched compound according to claim 1, wherein X is OH.

7. A method of using the enantiomerically enriched compound according to claim 1 as a chiral auxiliary to control the stereochemical outcome of a cycloaddition or a conjugate addition reaction.

8. The method according to claim 7, wherein the reaction is a cycloaddition reaction, which is a Diels-Alder reaction.

9. The method according to claim 8, wherein a suitable Lewis acid catalyst is used.

10. The method according to claim 9, wherein the Lewis acid catalyst is selected from the group consisting of $SnCl_4$, $AlCl_3$, $TiCl_4$, $BF_3$, $Et_2AlCl$ and $EtAlCl_2$.

11. A method of using the enantiomerically enriched compound according to claim 1 as a resolving agent to separate an enantiomer of a compound from a mixture of its enantiomers.

12. A method of using the enantiomerically enriched compound according to claim 1 to determine the stereochemistry of another compound.

13. A method of using the enantiomerically enriched compound according to claim 1 to determine the enantiomeric excess of a mixture of chiral compounds.

* * * * *